United States Patent
Kang et al.

(10) Patent No.: US 12,121,899 B2
(45) Date of Patent: Oct. 22, 2024

(54) PARALLEL MICROFLUIDIC DEVICE FOR HIGH THROUGHPUT CELL ASSAYS IN MICRODROPLETS

(71) Applicant: Northeastern University, Boston, MA (US)

(72) Inventors: Wenjing Kang, Waltham, MA (US); Tania Konry, Boston, MA (US); Saheli Sarkar, Boston, MA (US)

(73) Assignee: Northeastern University, Boston, MA (US)

( * ) Notice: Subject to any disclaimer, the term of this patent is extended or adjusted under 35 U.S.C. 154(b) by 939 days.

(21) Appl. No.: 17/261,992

(22) PCT Filed: Jul. 24, 2019

(86) PCT No.: PCT/US2019/043325
§ 371 (c)(1),
(2) Date: Jan. 21, 2021

(87) PCT Pub. No.: WO2020/023685
PCT Pub. Date: Jan. 30, 2020

(65) Prior Publication Data
US 2021/0308681 A1     Oct. 7, 2021

Related U.S. Application Data

(60) Provisional application No. 62/702,612, filed on Jul. 24, 2018.

(51) Int. Cl.
*B01L 3/00*     (2006.01)
*G01N 33/50*    (2006.01)

(52) U.S. Cl.
CPC .... *B01L 3/502784* (2013.01); *G01N 33/5005* (2013.01); *B01L 2200/028* (2013.01);
(Continued)

(58) Field of Classification Search
CPC ......... B01L 3/502784; B01L 2200/028; B01L 2200/0647; B01L 2200/0652; B01L 2300/0819; G01N 33/5005
See application file for complete search history.

(56) References Cited

U.S. PATENT DOCUMENTS

| 2015/0132837 A1 | 5/2015 | Frenz et al. |
| 2016/0298173 A1 | 10/2016 | Wang et al. |

(Continued)

FOREIGN PATENT DOCUMENTS

| WO | 2011112827 A2 | 9/2011 |
| WO | 2014107698 A1 | 7/2014 |

(Continued)

*Primary Examiner* — Jennifer Wecker
*Assistant Examiner* — Kathryn Elizabeth Limbaugh
(74) *Attorney, Agent, or Firm* — Verrill Dana, LLP

(57) ABSTRACT

A high throughput microdroplet-based system for single cell assays in microdroplets is provided. The system integrates parallel devices and switches to enable simultaneous analysis of different cells or cell combinations, or different assay conditions, on a single microfluidic chip. Interconnections between the inlets of individual devices on a common chip enable simultaneous screening of the effect of different combinations of drugs on single cells. The use of an oil inlet and microchannels with matched total flow resistance allows the synchronous generation of droplets with the same dimensions and/or volumes.

22 Claims, 15 Drawing Sheets

(52) U.S. Cl.
CPC .................. *B01L 2200/0647* (2013.01); *B01L 2200/0652* (2013.01); *B01L 2300/0819* (2013.01)

(56) References Cited

U.S. PATENT DOCUMENTS

| | | |
|---|---|---|
| 2017/0199173 A1 | 7/2017 | Konry et al. |
| 2018/0203005 A1 | 7/2018 | Konry et al. |
| 2018/0313844 A1 | 11/2018 | Konry et al. |

FOREIGN PATENT DOCUMENTS

| | | |
|---|---|---|
| WO | 2015139022 A1 | 9/2015 |
| WO | 2015200832 A1 | 12/2015 |
| WO | 2017011819 A1 | 1/2017 |
| WO | 2018013726 A1 | 1/2018 |

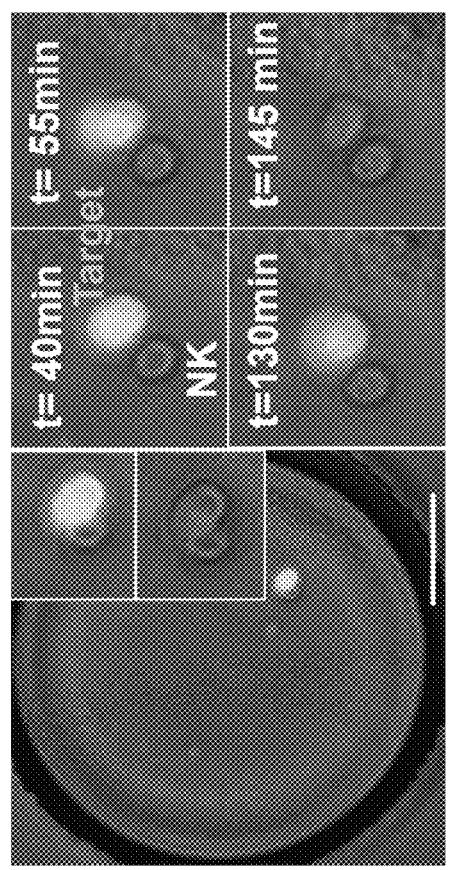
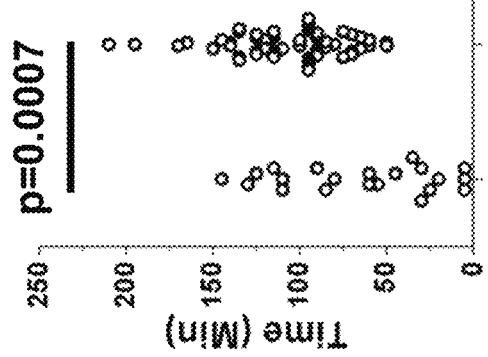
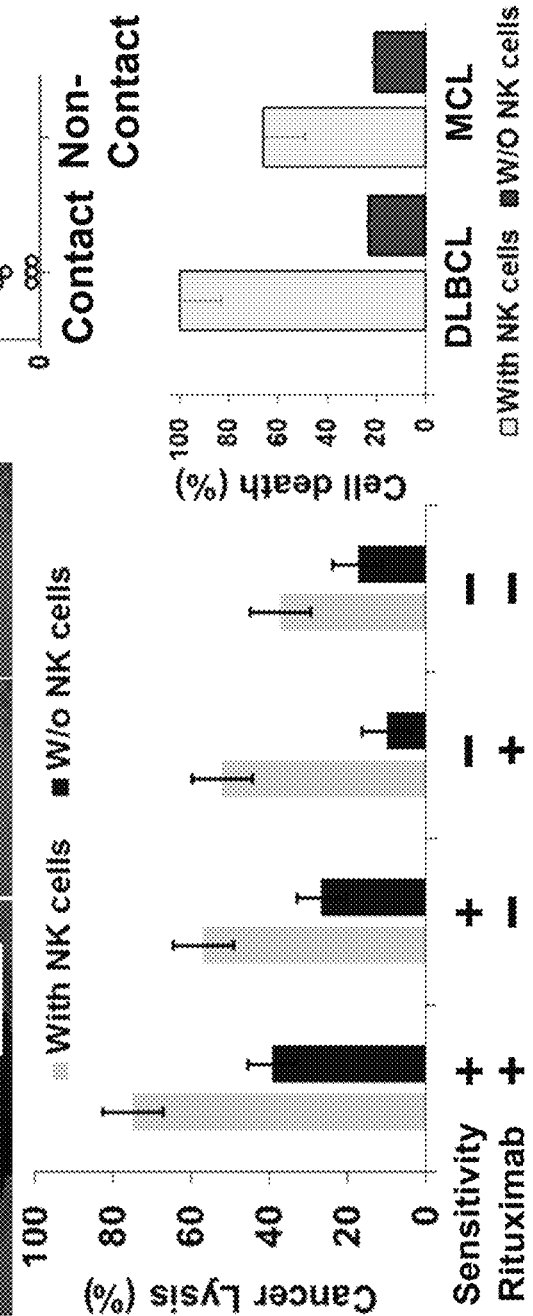
FIG. 7A
FIG. 7B
FIG. 7C
FIG. 7D

PARALLEL MICROFLUIDIC DEVICE FOR HIGH THROUGHPUT CELL ASSAYS IN MICRODROPLETS

CROSS REFERENCE TO RELATED APPLICATIONS

This application claims priority under 35 U.S.C. § 119(e) to U.S. Provisional Application No. 62/702,612, filed on Jul. 24, 2018, entitled "Parallel Droplet Microfluidic Device for Monitoring of Bacteria Culture and Multi-Drug Screening," the disclosure of which is hereby incorporated by reference.

BACKGROUND

Droplet-based microfluidic devices can be used to form and store droplets with desired dimensions in the microscale range, as well as to encapsulate single cells or groups of cells for analysis, drug screening, and real-time monitoring. Arrays of microdroplets are well suited for analysis of the susceptibility of cultured eukaryotic or prokaryotic cells to drugs or antimicrobial agents, and provide a better alternative to antimicrobial susceptibility testing (AST) methods that require longer analysis time and mammalian cells screenings to immunotherapy and drugs.

SUMMARY

The present technology can achieve higher throughput compared to previous microdroplet-based systems through use of a larger array with a higher droplet filling rate for screening. The technology integrates parallel devices and switches to enable simultaneous analysis of different cells or cell combinations, or different assay conditions such as presence or absence or different concentrations of modulatory factors, i.e., multiplex analysis on a single microfluidic chip. Interconnections between the inlets of individual devices on a common chip also enable simultaneous screening of the effect of different combinations of drugs on single eukaryotic and prokaryotic cells, including tumor cells and bacteria for screening of antitumor agents and antibiotics. The use of a simplified oil inlet and microchannels with matched total flow resistance allows the synchronous generation of droplets with the same dimensions and/or volumes. The devices of the present technology also provide droplet storage arrays for real-time monitoring via time-lapse microscopy. The present systems and devices can also include droplet sorting and droplet merging capabilities.

The following are aspects of the present technology.

1. A multiplex microfluidic system for analyzing cells in microdroplets, comprising:
   a chip comprising a plurality of microfluidic devices, each device comprising a microdroplet incubation chamber;
   an oil supply microchannel network in the chip comprising a plurality of microchannel branches fluidically connecting an inlet connectable to an oil supply and two or more of the microfluidic devices in the chip, the microchannel branches having substantially equal flow resistance;
   a cell supply microchannel network in the chip comprising a plurality of microchannel branches fluidically connecting one or more cell supply inlets connectable to a cell supply and two or more of the microfluidic devices in the chip, the microchannel branches having substantially equal flow resistance; and
   a plurality of droplet formation junctions in the chip, each droplet formation junction associated with one of the microfluidic devices and configured to produce aqueous microdroplets suspended in oil for delivery to the microdroplet incubation chamber, the aqueous microdroplets comprising at least one cell, each droplet formation junction comprising an intersection between one of the oil supply microchannel branches and at least one of the cell supply microchannel branches and an outgoing microchannel in fluid communication with the microdroplet incubation chamber.
2. The system of aspect 1, wherein each of the microchannel branches of the cell supply microchannel network has one or more parameters that are the same, the parameters selected from the group consisting of a length of the microchannel from the inlet to the droplet formation junction, a diameter of the microchannel from the inlet to the droplet formation junction, a material of the microchannel wall from the inlet to the droplet formation junction, a channel profile of the microchannel from the inlet to the droplet formation junction, and a pressure drop along the microchannel from the inlet to the droplet formation junction.
3. The system of aspect 1 or 2, wherein each of the microchannel branches of the oil supply microchannel network has one or more parameters that are the same, the parameters selected from the group consisting of a length of the microchannel from the inlet to the droplet formation junction, a diameter of the microchannel from the inlet to the droplet formation junction, a material of the microchannel wall from the inlet to the droplet formation junction, a channel profile of the microchannel from the inlet to the droplet formation junction, and a pressure drop along the microchannel from the inlet to the droplet formation junction.
4. The system of any of the preceding aspects, wherein the intersection of each droplet formation junction is disposed between at least one of the oil supply microchannel branches and at least two of the cell supply microchannel branches, and wherein the outgoing microchannel is in fluid communication with the microdroplet incubation chamber.
5. The system of any of the preceding aspects, further comprising a cell suspension fluidically connected with the one or more cell supply inlets, wherein the cell suspension comprises a cell type selected from tumor cells, immune cells, natural killer cells, T cells, B cells, dendrocytes, macrophages, and bacterial cells.
6. The system of any of the preceding aspects, further comprising a plurality of different cell supply inlets, each in fluid communication with one or more additional microchannel branches of substantially equal flow resistance, each branch intersecting at an upstream junction with associated ones of the branches of the cell supply microchannel network upstream of the droplet formation junction with the oil supply microchannel branches.
7. The system of aspect 6, further comprising a first cell suspension fluidically connected with the one or more cell supply inlets and a second cell suspension fluidically connected to the additional cell supply microchannel network, wherein each of the first and second cell suspensions comprises a cell type selected from the group consisting of tumor cells, immune cells, natural killer cells, T cells, B cells, dendrocytes, macrophages, and bacterial cells.

8. The system of any of the preceding aspects, further comprising a reagent supply microchannel network in fluid communication with at least two reagent solutions having different reagent concentrations, the reagent supply microchannel network comprising a mixing pathway of interconnected microchannels to provide mixtures having different reagent concentrations, the interconnected microchannels intersecting at upstream junctions with the microchannel branches of the cell supply microchannel network upstream of the droplet formation junction with the oil supply microchannel branches.

9. The system of any of the preceding aspects, wherein the oil supply microchannel network includes a single oil supply inlet formed in the chip, and each of the microchannel branches of the oil supply microchannel network extends through the chip from the single oil supply inlet to an associated one of the droplet formation junctions.

10. The system of any of the preceding aspects, wherein the oil supply microchannel network includes a plurality of oil supply inlets formed in the chip, and at least two microchannel branches of the oil supply microchannel network extend through the chip from one of the plurality of oil supply inlets.

11. The system of any of the preceding aspects, wherein the incubation chamber comprises an array of single microdroplet chambers or an array of microdroplet docking stations.

12. The system of any of the preceding aspects, comprising at least six of the microfluidic devices.

13. The system of any of the preceding aspects, comprising at least eight of the microfluidic devices.

14. The system of any of the preceding aspects, further comprising a microdroplet sorter on a microchannel of at least one of the microfluidic devices, the sorter configured to sort microdroplets from the microfluidic device into at least a first subgroup of microdroplets having a first characteristic and a second subgroup of microdroplets having a second characteristic.

15. The system of aspect 14, wherein said first and second characteristics are selected from the presence or absence of one or more cell types or cell combinations, the presence of one or more cell biomarkers, living or dead cell condition, cell staining, and cell morphology.

16. The system of aspect 14 or 15, wherein said microdroplet sorter is configured to direct said first and second subgroups of microdroplets into different downstream microdroplet incubation chambers.

17. The system of aspect 14 or 15, wherein the microdroplet sorter is configured to deliver microdroplets of interest to the midroplet incubation chamber or to another on chip or off chip microfluidic device, and to direct microdroplets not of interest to a waste pathway.

18. The system of aspect 16 or 17, wherein microdroplets of interest are directed to the microdroplet incubation chamber, further comprising a second microdroplet sorter downstream of said microdroplet incubation chamber and configured to sort droplets exiting the microdroplet incubation chamber according to one or more cell characteristics, and to direct microdroplets to a merging junction configured to merge the microdroplets with microdroplets containing a reagent of cell of interest, to a second microdroplet incubation chamber, or to a collection port.

19. The system of any of the preceding aspects, further comprising a merging junction configured to merge microdroplets in a microchannel of a microfluidic device with microdroplets containing a reagent or cell of interest.

20. A method of multiplex analysis of single cell characteristics, the method comprising:
    (a) providing the multiplex microfluidic system of any of the preceding aspects, an oil, at least a first suspension of single cells, and optionally at least a first reagent;
    (b) flowing the oil and the cell suspension into their respective inlets in the chip, so as to form two or more streams of aqueous microdroplets in the oil at the droplet formation junctions of the chip, at least a portion of the microdroplets containing one or more cells per microdroplet, whereby the microdroplets enter respective microdroplet incubation chambers of the microfluidic devices;
    (c) incubating the microdroplets in the microdroplet incubation chambers to allow expression of one or more cell characteristics of cells within the microdroplets; and
    (d) analyzing said single cell characteristics by observing the microdroplets during step (c).

21. The method of aspect 20, further comprising (e) harvesting microdroplets from the microdroplet incubation chambers after step (d).

22. The method of aspect 21, further comprising culturing or analyzing cells from the harvested microdroplets.

23. The method of aspect 22, wherein said analyzing comprises single cell nucleic acid sequencing.

24. The method of any of aspects 20-23, wherein the system of aspect 6 and a second suspension of single cells, different from the first cell suspension, are provided in step (a), wherein at least a portion of the formed microdroplets contain one or more cells from the first suspension and one or more cells from the second suspension, and wherein interactions between cells of the first suspension and cells of the second suspension are analyzed in step (d).

25. The method of any of aspects 20-24, wherein two or more microfluidic devices of the multiplex microfluidic system comprise microdroplets containing different cells or different mixtures of cells in steps (b), (c), and (d).

26. The method of any of aspects 20-25, wherein two or more microfluidic devices of the multiplex microfluidic system comprise microdroplets containing different cells or different mixtures of cells in steps (b), (c), and (d).

27. The method of aspect 26, wherein the first cell suspension comprises target cells and the second cell suspension comprises immune cells.

28. The method of aspect 27, wherein the target cells are tumor cells or microbial cells.

29. The method of aspect 27 or 28, wherein the target cells and immune cells are isolated from the same subject.

30. The method of any of aspects 27-29, wherein the analysis of step (d) comprises ascertaining whether the target cells are killed by the immune cells.

31. The method of aspect 20, wherein the system of aspect 8 and said at least two reagent solutions having different reagent concentrations are provided in step (a), wherein a plurality of reagent solutions are generated in the reagent supply microchannel network and each reagent solution has a different reagent concentration and is delivered by a separate microchannel to the droplet forming junction of a unique one of the microfluidic devices of the chip; and wherein the effect of each of said reagent concentrations on the cells is analyzed in step (d).
32. The method of aspect 31, wherein the analysis of step (d) comprises ascertaining whether the cells are killed by the reagent.
33. The method of aspect 20, wherein the system of aspect 19 and a solution comprising one or more reagents and/or one or more additional cells are provided in step (a), and wherein the one or more reagents or one or more additional cells are added to microdroplets within the system at the merging junction.
34. The method of aspect 33, wherein the merging junction is disposed upstream of a microdroplet incubation chamber, and an effect of the added reagent(s) and/or additional cell(s) is analyzed in step (d).
35. The method of aspect 20, wherein the system of any of aspects 14-18 is provided and microdroplets are sorted based on the analysis performed in step (d).
36. The method of aspect 20, wherein the system of any of aspects 14-18 is provided, and wherein microdroplets are sorted based on presence or absence of one or more biomarkers in cells contained in the microdroplets as analyzed by the sorter.
37. The method of aspect 36, wherein the sorting is performed between steps (b) and (c) so as to enrich a population of microdroplets entering the microdroplet incubation chamber in microdroplets comprising cells of interest.
38. The method of aspect 20, wherein the system of aspect 18 is provided, and wherein the method further comprises between steps (b) and (c):
  (b1) using the first sorter to enrich microdroplets containing combinations of cells of interest prior to entry of the sorted microdroplets into the microdroplet incubation chamber; and further comprises after step (d):
  (e) using the second sorter to sort microdroplets exiting the microdroplet incubation chamber according to results of the analysis performed in step (d);
  (f) optionally merging the microdroplets obtained from step (e), or a portion thereof, with microdroplets containing a reagent or additional cells; and
  (g) flowing the microdroplets resulting from step (f) into a second microdroplet incubation chamber;
  (h) incubating the microdroplets in the second microdroplet incubation chamber to allow expression of one or more cell characteristics of cells within the microdroplets; and
  (i) analyzing said single cell characteristics by observing the microdroplets during step (h).
39. The method of aspect 38, further comprising (j) harvesting microdroplets from the second microdroplet incubation chamber after step (i).
40. The method of aspect 39, further comprising culturing or analyzing cells from the harvested microdroplets.
41. The method of aspect 40, wherein said analyzing comprises single cell nucleic acid sequencing.
42. A microdroplet sorting and analysis chip comprising:
  an oil supply microchannel fluidically connecting an oil supply inlet to a droplet formation junction configured to form a plurality of aqueous microdroplets;
  a cell supply microchannel fluidically connecting one or more cell supply inlets to the droplet formation junction;
  a first microdroplet sorter disposed downstream of the droplet formation junction, the sorter configured to sort microdroplets from the droplet formation junction according to one or more characteristics of cells present in the microdroplets, wherein the sorted microdroplets are diverted into one of two or more microchannels exiting the first sorter;
  a first microdroplet incubation chamber disposed downstream of one or more of the microchannels exiting the first sorter;
  a second microdroplet sorter disposed downstream of the first microdroplet incubation chamber, the second sorter configured to sort microdroplets exiting the first microdroplet incubation chamber according to one or more characteristics of cells present in the microdroplets, wherein the sorted microdroplets are diverted into one of two or more microchannels exiting the second sorter;
  an optional microdroplet merging junction configured to merge at least a portion of the microdroplets obtained from the second sorter with aqueous microdroplets comprising a reagent and/or additional cells;
  a second microdroplet incubation chamber disposed downstream of one or more of the microchannels exiting the second sorter or downstream of the microdroplet merging junction, if present.
43. A method of sorting and analyzing cells in microdroplets, the method comprising:
  (a) providing the microdroplet sorting and analysis chip of aspect 42, an oil, at least a first suspension of single cells, and optionally at least a first reagent and/or a suspension of additional single cells;
  (b) flowing the oil and the first cell suspension into their respective inlets in the chip, so as to form a stream of aqueous microdroplets in the oil at the droplet formation junction, at least a portion of the microdroplets containing one or more cells per microdroplet;
  (c) sorting the microdroplets from (b) at the first sorter according to one or more characteristics of cells in the microdroplets, whereby at least a portion of the microdroplets flow into the first microdroplet incubation chamber;
  (d) incubating the microdroplets in the first microdroplet incubation chamber to allow expression of one or more cell characteristics of cells within the microdroplets;
  (e) analyzing said single cell characteristics by observing the microdroplets during step (d);
  (f) flowing the microdroplets from the first microdroplet incubation chamber to the second sorter and sorting the microdroplets using the second sorter according to one or more characteristics of cells in the microdroplets, whereby (i) at least a portion of the microdroplets flow into the optional droplet merging junction and merge with microdroplets containing said first reagent and/or said suspension of additional single cells and the merged droplets flow into the second microdroplet incubation chamber, or (ii) at least a portion of the microdroplets flow into the second microdroplet incubation chamber;
  (g) incubating the microdroplets in the second microdroplet incubation chamber to allow expression of one or more characteristics of cells within the microdroplets; and
  (h) analyzing said cell characteristics by observing the microdroplets during step (g).

44. The method of aspect 43, further comprising (i) harvesting microdroplets from the second microdroplet incubation chamber after step (h).
45. The method of aspect 44, further comprising culturing or analyzing cells from the harvested microdroplets.
46. The method of aspect 45, wherein said analyzing comprises single cell nucleic acid sequencing.

DESCRIPTION OF THE DRAWINGS

FIG. 3B is a schematic illustration of the upstream sorter of FIG. 3A, in which regular IDTs are used to achieve in-droplet alignment and SPFTs are applied to sort droplets based on fluorescence.

FIGS. 7A-7D illustrate an example of NK cell-target cell dynamic interaction in microdroplets. FIG. 7A is a series of images illustrating contact between NK and target (SUDHL10) cells ending in death of the target cell. FIG. 7B illustrates heterogeneity in lymphoma cell death due to contact-dependent and contact-independent mechanisms mediated by NK cells in droplets. FIG. 7C illustrates the death of rituximab-sensitive and rituximab-resistant cells in the presence of NK cells. FIG. 7D illustrates patient derived lymphoma cell death in microdroplets in the presence and absence of NK cells.

DETAILED DESCRIPTION

Figure 1A:
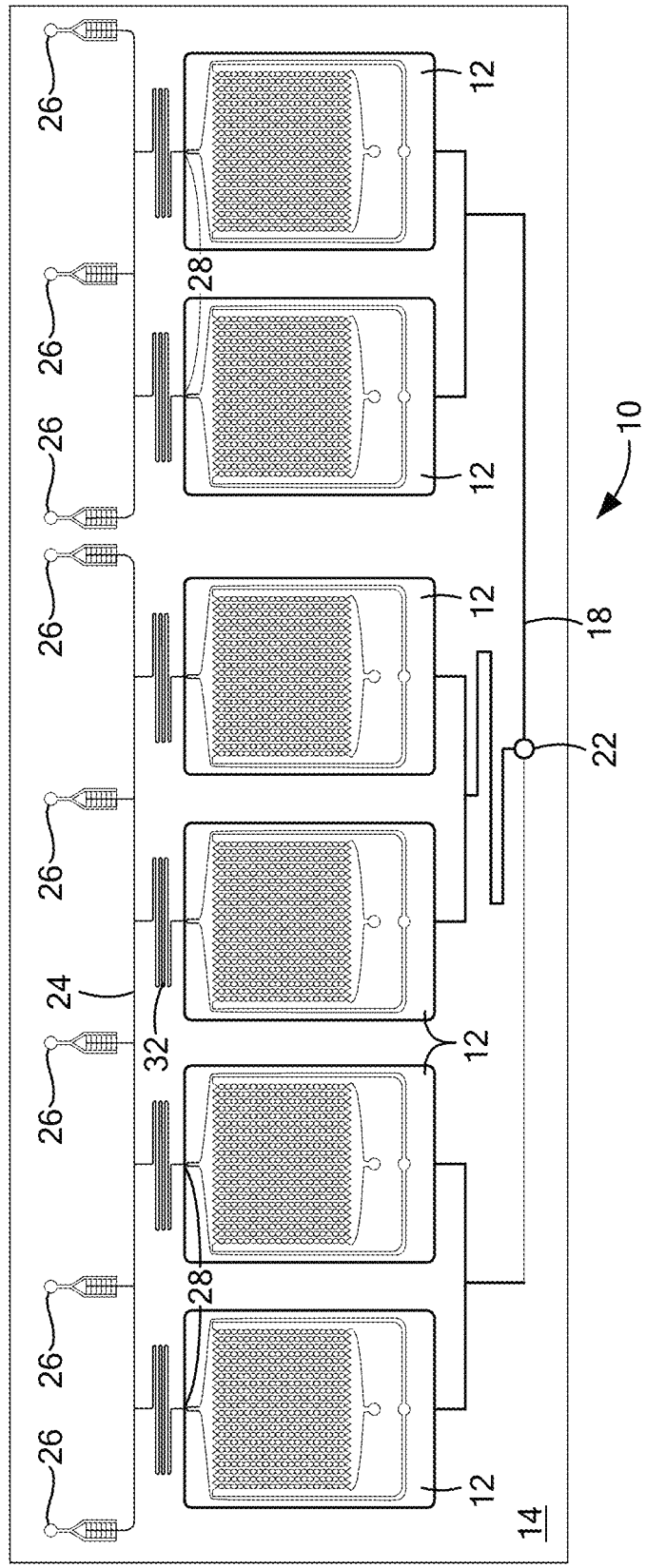
FIG. 1A is a schematic illustration of an aspect of a multiplex microfluidic system.

Microfluidic devices of the present technology provide high-throughput, high-efficiency single cell drug screening applications for use in the pharmaceutical industry. Large quantities of eukaryotic or bacterial cells can be incubated on chip in various controlled environments in a laboratory. The present technology provides a droplet-based microfluidic system allowing single-cell resolution imaging of cell interactions and measurement of cell secretions in response to specific stimulation.

In some aspects, the technology can provide for simultaneous multi-parametric assessment of live single cell analysis and live cell-cell interactions in dynamics. The technology can integrate the developed platform for investigation of functional phenotype and synaptic communication as well as functional outcome of interacting cell pairs. The technology can quantify the efficacy of cell-based immunotherapies based on variable levels of function analysis.

Immune cell therapy has the potential to improve the burden of chronic and progressive diseases. To improve the therapeutic use of immune cell vaccination strategies it is important to understand the biology of these vaccines and their regulation mechanisms of the innate and adaptive immune systems. Single cell dynamic analysis tools have potential as preclinical and/or experimental in vitro models to provide a better understanding of biological heterogeneity, thereby to create more efficient therapies for translational applications. Quantitative single-cell analysis of cell communication and activity, coupled with phenotypic screening of distinct subsets of cells from a mixed cell population, has the potential to correlate functional heterogeneity observed in each subset with the corresponding molecular signatures. However, no existing analytical platform combines all of these experimental approaches into a comprehensive and analytical/integrated approach.

The technology described herein can help to address this unmet need in the field of biomedical analysis. The technology herein provides a multifunctional microfluidic droplet-based approach to identify functionally distinct single cells. Thus, each droplet can be used as a bioreactor or a "test tube" for ultra-fast multiple bio-reactions for quantitative analysis of phenotypic responses, while using minimum amounts of the bioassay reagents. The technology can provide tracking of cell responses from the time of initiation of their interaction, because the effector and target cells are separated from each other prior to interaction in droplets. Thus, the history of cell response can be profiled from its beginning to the end point of the assay. This allows correlation of the temporal dynamics of polyfunctional responses and establishes the biological order of events such as initiation of contact, synaptic communication, cytokine release, and apoptosis using fluorescent-based bioassays.

Devices and systems that provide robust droplet platforms to enable generation of an array of droplets with live single or multiple cell types are described in WO 2011/112827, WO 2014/107698, WO 2015/139022, WO/2015/200832, WO/2017/011819, and US 2018/0313844, the disclosures of which are incorporated by reference herein.

Chip design improvements of the present technology include integration of larger arrays to guarantee sufficient droplets for screening, and integrating at least two parallel designs to achieve multiplexing capabilities. In the parallel device designs, interconnections between the inlets of individual devices enable screening of different combinations of drugs and/or different concentrations of drugs and/or different cells using a single chip containing two or more multiple droplet storage arrays. The system described herein can simplify the number of oil inlets required and create channels with unified or substantially unified flow resistance, for example, by maintaining equal path lengths and identical channel diameters, profiles, and materials, for synchronous generation of droplets with the same dimensions and volumes.

Some aspects of the present system utilize an array of six devices on a standard 1×3 inch microscope slide, which provides simultaneous monitoring of several samples and/or several test substances. This provides advantages over previous droplet-based microfluidic devices that contain two analyte inlets, allowing the user to study only the interaction of one type of cell with one drug, or the interaction of only two cell types. In order to reduce the number of inlets and outlets, the flow from certain inlets is divided to supply multiple devices on a single chip, and oil is supplied by a single inlet and shared among several devices. Certain inlets are interconnected so that one sample can be supplied to and tested in two devices simultaneously, which allows a single cell type to be tested with several analytes or several concentrations of a single analyte, or combinations of two or more different analytes each at two or more different concentrations, on a single device. In some aspects, by manipulating the input cell types as well as the initial cell densities, it is possible to obtain droplets with one cell, two cells, and three cells, as well as multiple cells of one type. This increases the versatility of the technology by allowing the study of sequential and simultaneous cell communications.

Device fabrication and operation protocols can be optimized and established. Parameters such as flow rates for each segment of the integrated merging and array, selection of oil for optimal droplet stability during docking and merging, and the appropriate surfactant necessary as well as the correct concentration can be determined experimentally. The conditions which allow minimal shrinkage and cell death of each proposed cell type in the droplets can be selected.

Figure 1B:
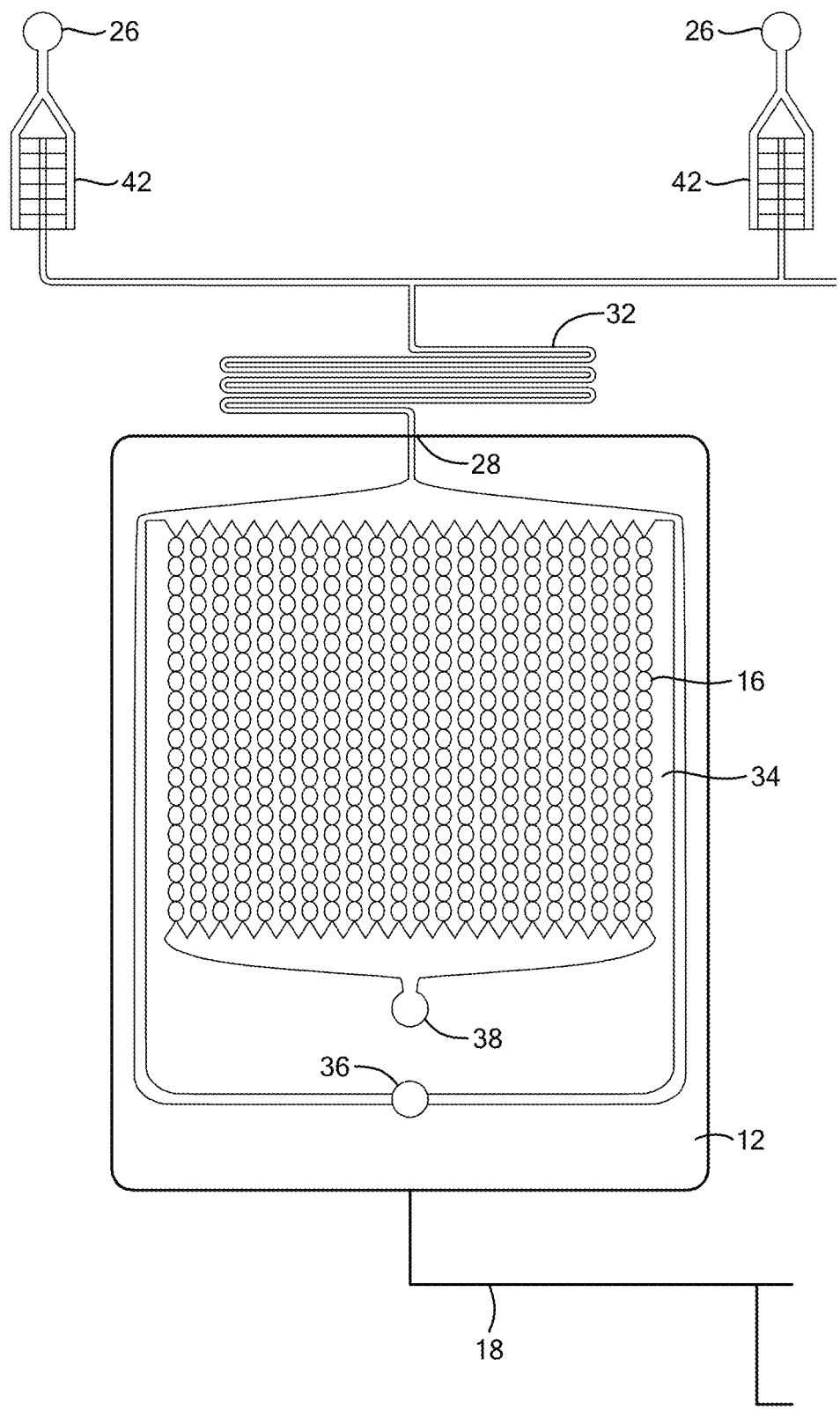
FIG. 1B is a partial schematic illustration of a microfluidic device of the multiplex microfluidic system of FIG. 1A.

FIGS. 1A and 1B illustrate an aspect of a multiplex microfluidic system 10 for analyzing cells in microdroplets that includes six interconnected individual devices 12. More particularly, the system includes a chip 14 having a plurality of microfluidic devices 12. Each microfluidic device includes a microdroplet incubation chamber 16. A representative individual microfluidic device is shown in FIG. 1B. An oil supply microchannel network 18 in the chip provides fluidically connected microchannel branches between an oil inlet 22 connectable to an oil supply and each of the microfluidic devices 12 in the chip. The oil supply microchannel branches can provide a substantially equal resistance to the fluid flow therefrom from the inlet to the microfluidic devices in the chip. A cell supply microchannel network 24 in the chip provides fluidically connected microchannel branches between one or more cell supply inlets 26 connectable to a cell supply and each of the microfluidic devices 12 in the chip. The cell supply microchannel branches can also provide a substantially equal resistance to the fluid flow therefrom from the inlet to the microfluidic devices in the chip.

A plurality of droplet formation junctions 28 or droplet generators are provided in the chip. Each droplet formation junction is associated with one of the microfluidic devices and configured to produce aqueous droplets suspended in oil for delivery to the microfluidic device, the aqueous droplets comprising at least one cell, each droplet formation junction comprising an intersection between one of the oil supply microchannel branches and at least one of the cell supply microchannel branches and an outgoing microchannel in fluid communication with the associated microfluidic device.

Referring to FIGS. 1A and 1B, each device includes an optional serpentine mixer 32 for equally mixing fluids from two laminar flows upstream of the flow-focusing droplet generator 28, followed by the incubation chamber, which can be a docking array 34 for housing up to one thousand droplets, or several thousand droplets, such as about 2000 or more, 3000 or more, 4000 or more, 5000 or more, 6000 or more, 7000 or more, 8000 or more, 9000 or more, or 10000 or more droplets. The droplets (also referred to herein as microdroplets) have diameters in the micrometer range (i.e., from 1-1000 μm). Some inlets are for one device exclusively, while others are shared, delivering the same analyte to two or more devices. The oil channels can be designed (e.g., having the same channel diameter, profile, and material) to ensure equal flow resistance and thus equal flow rate from the oil inlet to each flow-focusing junction, so that the dimensions and/or volumes of the droplets in each device remain the same. Two outlets can be included for each device, one outlet 36 for discarding waste solution and undesired droplets, the other outlet 38 for use when filling and/or emptying the array. Optional filter 42 can be provided downstream of the inlets 26, for example, to remove debris.

The device can be fabricated using a soft-lithography approach, which involves casting silicone elastomer onto a master template formed by cross-linked photoresist on a silicon wafer or other rigid material. The elastomer replica is then bonded to a clean, flat substrate, such as a glass microscope slide, after inlets and outlets are prepared. When the device is firmly bonded, tubing or other supply lines can be connected to pumps or syringes (driven by accurately controlled syringe pumps) which contain samples such as cells or drugs. Assays of cell function or drug effects can be carried out using parallel mixing or dilution of drug solutions, generation of droplets containing encapsulated eukaryotic (such as human or other mammalian) cells or bacteria, and loading and storage of the droplets into all six devices, followed by time-lapse microscopy.

Chemotherapeutic drugs and monoclonal antibodies can have significant effects on immune cell functions. Further multiplexed microfluidic chip embodiments are shown in FIGS. 2A-2C, which can be used to analyze cell functions.

Figure 2A:
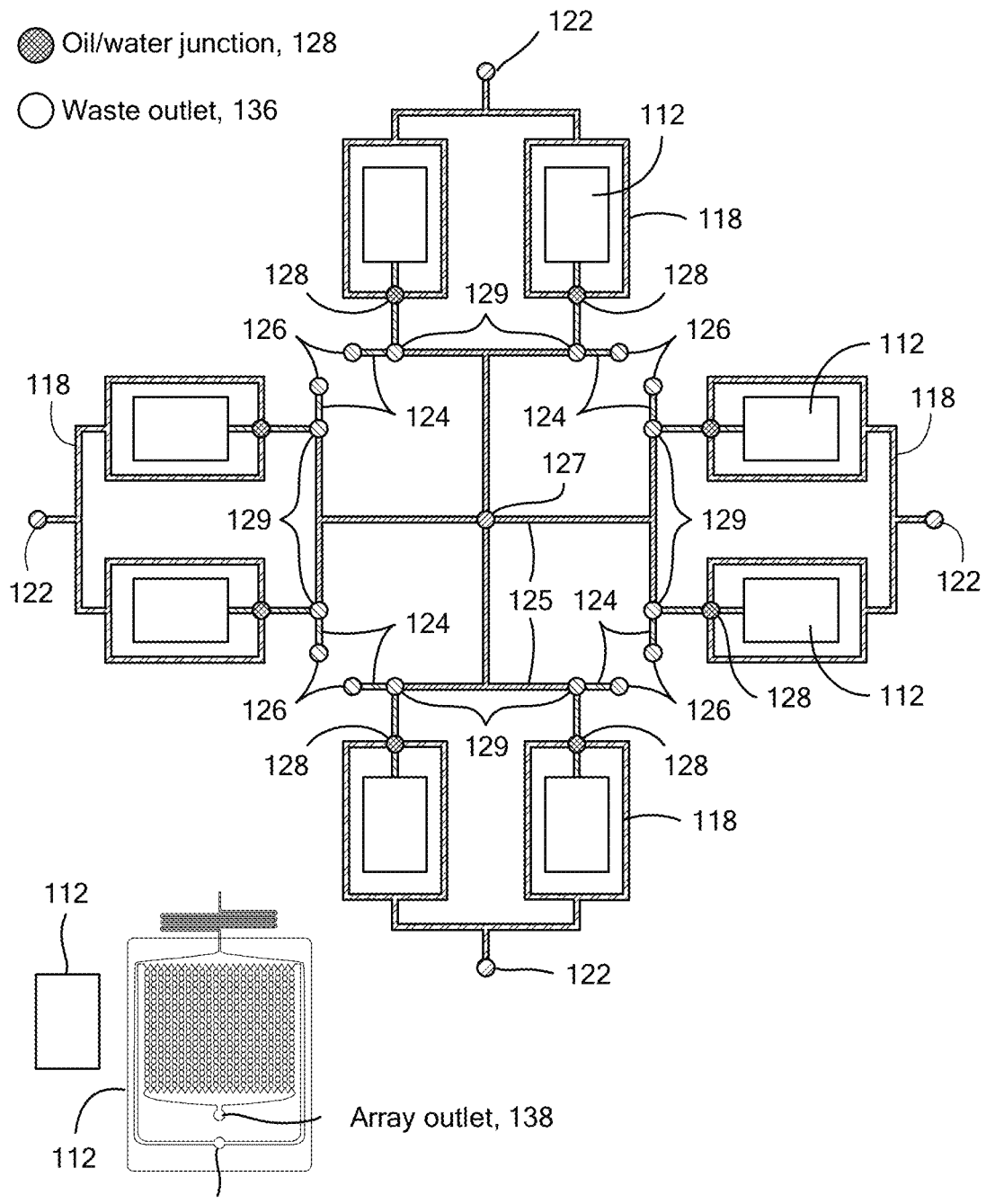
FIG. 2A is a schematic illustration of a multifluidic system incorporating a multiplexed microdroplet chip configuration, in which the chip can incorporate eight different therapeutic cell lines against one clinical specimen (i.e., target cell source).
Figure 2B:
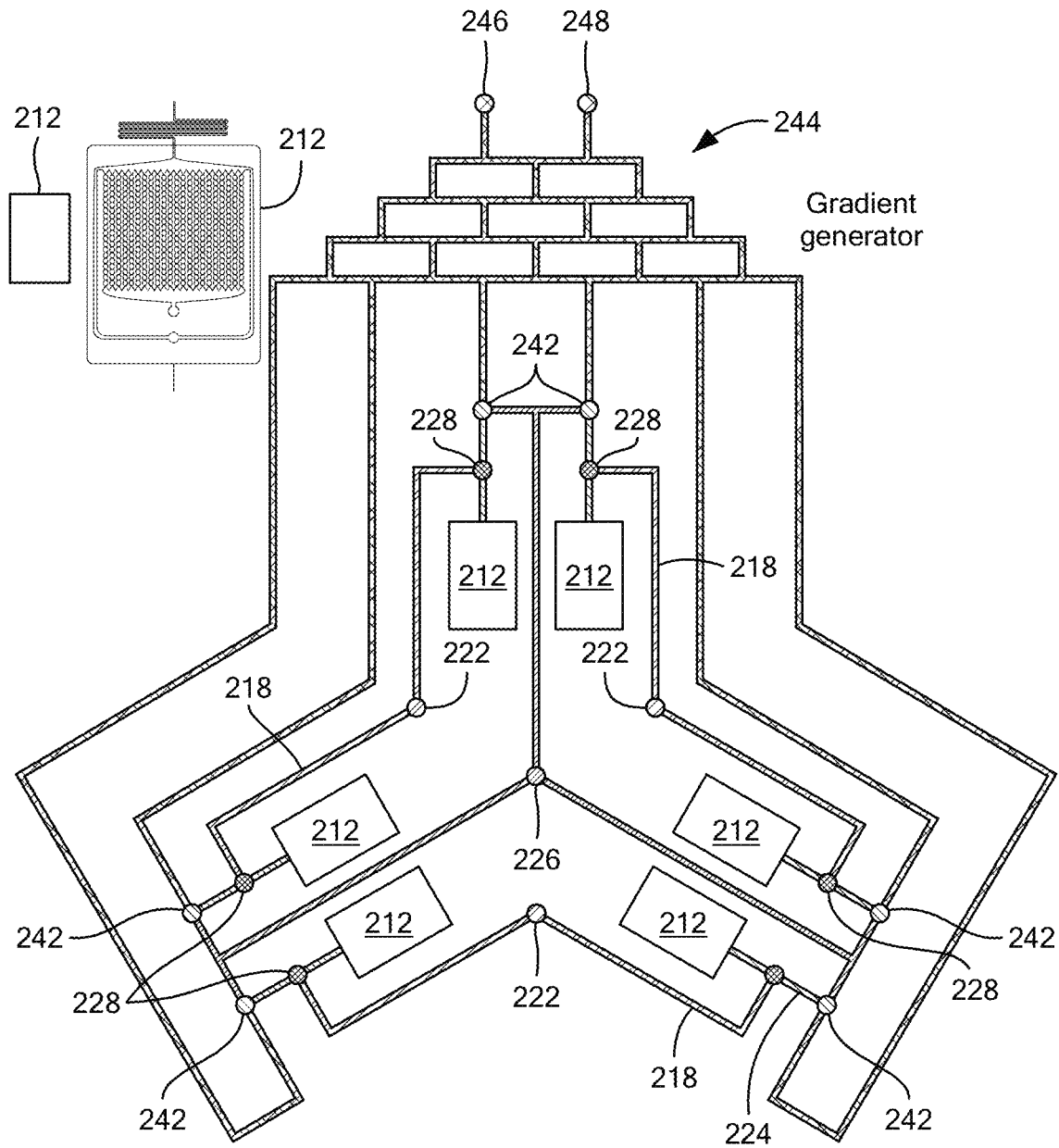
FIG. 2B is a schematic illustration of a microfluidic system that combines on-board drug dilution with droplet formation, enabling generation of different drug concentrations in six independent incubation arrays; this can be used to determine a dose-response curve in a single experiment at the single cell level.
Figure 2C:
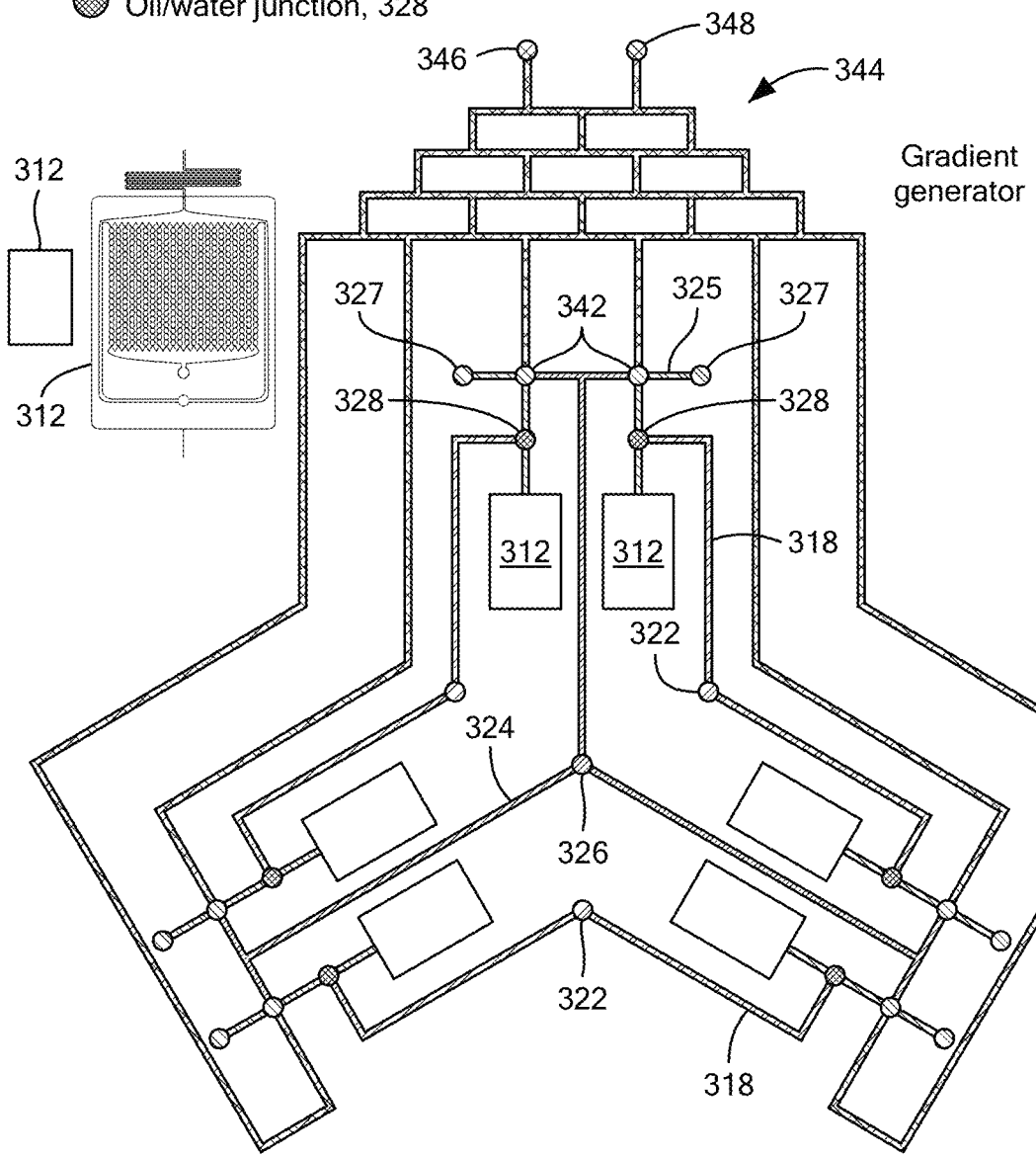
FIG. 2C is a schematic illustration of a further microfluidic system that combines on-board drug dilution with droplet formation, enabling generation of different drug concentrations in six independent incubation arrays.

FIG. 2A shows a chip designed to incorporate eight different therapeutic cell lines for study against cells derived from one clinical specimen (e.g., a tumor). The chip includes eight microfluidic devices 112, each of which includes a microdroplet incubation chamber 116.

An oil supply microchannel network 118 in the chip provides fluidically connected microchannel branches between an oil inlet or inlets 122 connectable to an oil supply and each of the microfluidic devices 112 in the chip. Four oil inlets 122 are shown in FIG. 2A; one oil inlet includes microchannel branches leading to two associated microfluidic devices. The oil supply microchannel branches provide a substantially equal resistance to the fluid flow therefrom from the inlets to the microfluidic devices in the chip.

A cell supply microchannel network 124 in the chip provides fluidically connected microchannel branches between one or more cell supply inlets 126 connectable to a cell supply and each of the microfluidic devices 112 in the chip. An additional cell supply microchannel network 125 is provided in fluid communication with one or more additional cell supply sources. The additional cell supply microchannel network 125 includes additional microchannel branches from one or more additional cell supply inlets 127. Each branch intersects at an upstream junction 129 with associated ones of the branches of the cell supply microchannel network 124. The upstream junction 129 is disposed upstream of a droplet formation junction 128 with the oil supply network microchannel branches 118. The cell supply and additional cell supply microchannel branches provide a substantially equal resistance to the fluid flow therefrom from the inlets to the microfluidic devices in the chip. Each device can include a waste outlet 136 and an array outlet 138.

A plurality of droplet formation junctions 128 or droplet generators are provided in the chip. Each droplet formation junction (also termed oil/water junction or oil/aqueous junction) is associated with one of the microfluidic devices and configured to produce aqueous droplets suspended in oil for delivery to the microfluidic device, the aqueous droplets comprising at least one cell. Each droplet formation junction is formed at an intersection between one of the oil supply microchannel branches 118 and at least one of the cell supply microchannel branches 124, 125 and an outgoing microchannel in fluid communication with the associated microfluidic device.

For example, in the system of FIG. 2A, target cells (e.g., dispersed tumor cells) can be input at inlet 126, and mixed at a mixing junction 129 with NK cells fed in from inlet 127. The mixed cell suspension can be formed into microdroplets in oil, fed in from oil inlet 132, at oil/water or droplet formation junction 128. The cell-containing microdroplets can be organized into arrays and stored within droplet arrays in the microfluidic devices 112.

FIG. 2B shows a design of a microfluidic device that combines automatic onboard drug dilution with droplet formation, enabling generation of different drug concentrations in six independent incubation arrays.

An oil supply microchannel network 218 in the chip provides fluidically connected microchannel branches between an oil inlet or inlets 222 connectable to an oil supply and each of the microfluidic devices in the chip. Three oil inlets are shown in FIG. 2B; one oil inlet includes microchannel branches leading to two associated microfluidic devices. The oil supply microchannel branches provide a substantially equal resistance to the fluid flow therefrom from the inlets to the microfluidic devices in the chip.

A cell supply microchannel network 224 in the chip provides fluidically connected microchannel branches between one or more cell supply inlets 226 connectable to a cell supply and each of the microfluidic devices 212 in the chip. A further cell supply microchannel network is provided in fluid communication with at least two drug supply sources 246, 248. The further cell supply microchannel network 244 provides a gradient generator formed as a mixing pathway of interconnected microchannels to provide mixtures having different concentrations, the interconnected microchannels intersecting at upstream junctions 242 with the microchannel branches of the cell supply microchannel network upstream of a droplet formation junction 228 with the oil supply microchannel branches.

The upstream junction is disposed upstream of a droplet formation junction with the oil supply microchannel branches. A plurality of droplet formation junctions or droplet generators are provided in the chip. Each droplet formation junction is associated with one of the microfluidic devices and configured to produce aqueous droplets suspended in oil for delivery to the microfluidic device, the aqueous droplets comprising at least one cell, each droplet formation junction comprising an intersection between one of the oil supply microchannel branches and at least one of the cell supply microchannel branches and an outgoing microchannel in fluid communication with the associated microfluidic device.

For example, in the system of FIG. 2B, high and low concentrations of a drug are introduced at two inlets 246, 248, and fed through a mixing pathway 244 to result in six different drug concentrations being automatically generated. Each drug solution, having a unique concentration, is led to the junction 242 where it is mixed with cells, such as bacteria cells, that were input at inlet 226. The suspension containing the drug/cell mixture is formed into microdroplets in oil at junction 228, and the microdroplets arranged and stored within arrays 212.

FIG. 2C shows a further design of a microfluidic device that combines automatic onboard drug dilution with droplet formation, enabling generation of different drug concentrations in combination with, for example, a target cell and an immune cell, in six independent incubation arrays.

An oil supply microchannel network 318 in the chip provides fluidically connected microchannel branches between an oil inlet or inlets 322 connectable to an oil supply and each of the microfluidic devices in the chip. Three oil inlets are shown in FIG. 2C; one oil inlet includes microchannel branches leading to two associated microfluidic devices. The oil supply microchannel branches provide a substantially equal resistance to the fluid flow therefrom from the inlets to the microfluidic devices in the chip.

A cell supply microchannel network 324 in the chip provides fluidically connected microchannel branches between one or more cell supply inlets 326 connectable to a cell supply and each of the microfluidic devices 312 in the chip. An additional cell supply microchannel network is provided in fluid communication with one or more additional cell supply sources. The additional cell supply microchannel network 325 includes additional microchannel branches, each branch intersecting at an upstream junction 342 with associated ones of the branches of the cell supply microchannel network. A further cell supply microchannel network 344 is provided in fluid communication with at least two drug supply sources 346, 348. The further cell supply microchannel network provides a gradient generator formed as mixing pathway of interconnected microchannels to provide mixtures having different concentrations, the interconnected microchannels intersecting at the upstream junctions 342 with the microchannel branches of the cell supply microchannel network 326 and additional cell supply microchannel network 325 upstream of the droplet formation junction 328 with the oil supply microchannel branches.

For example, in the system of FIG. 2C, high and low concentrations of a drug are introduced at two inlets 346, 348, and fed through a mixing pathway 344 to result in six different drug concentrations being automatically generated. Each drug solution, having a unique concentration, is led to the junction 342 where it is mixed with cells, such as target cells input at inlet 327 and NK cells input at inlet 326. The suspension containing the drug/cell mixture is formed into microdroplets in oil at junction 328, and the microdroplets arranged and stored within arrays 312.

Figure 2D:
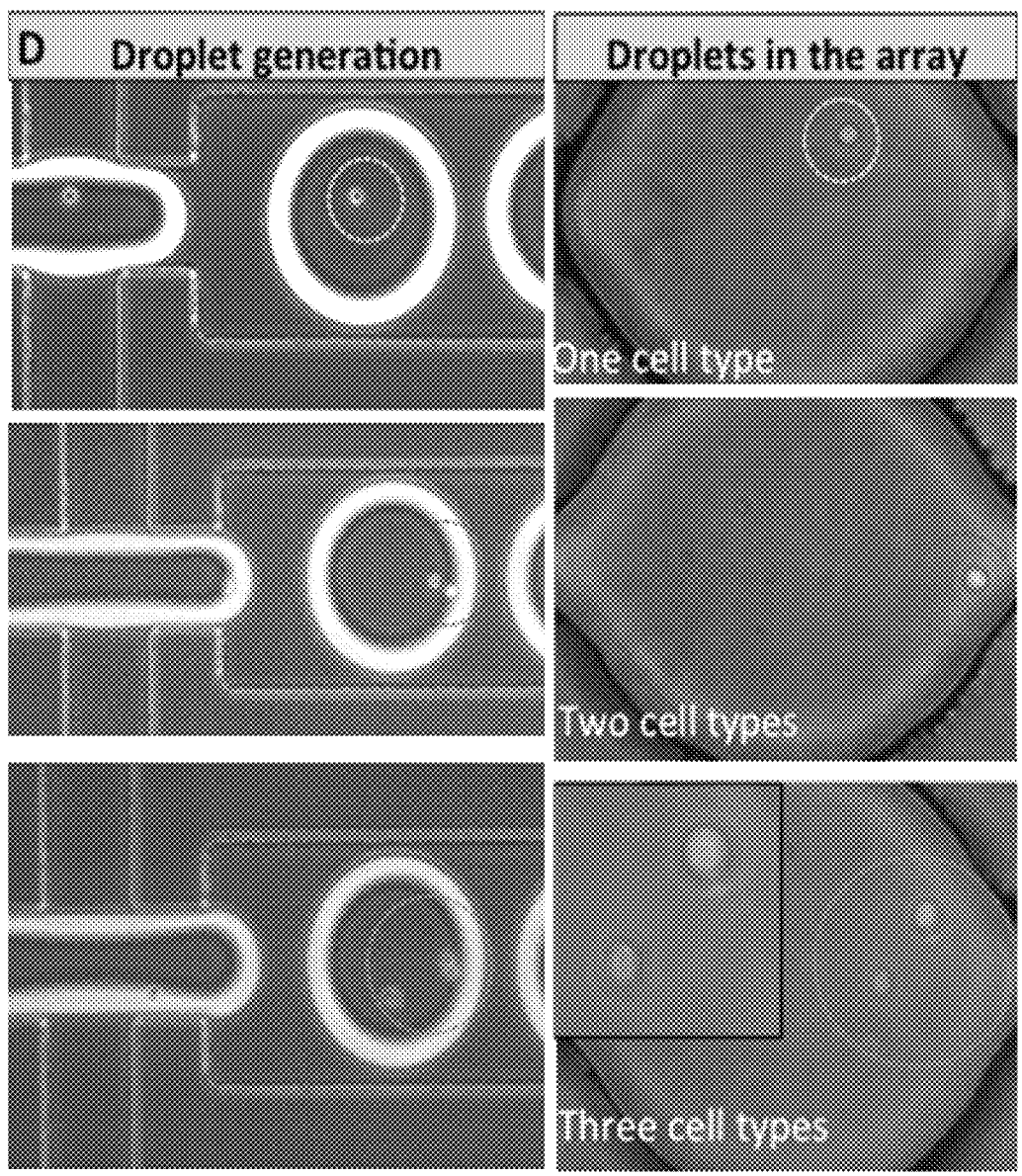
FIG. 2D is a series of images illustrating single cell encapsulation and co-encapsulation of two and three cell types in a single droplet.

FIG. 2D shows results of single cell encapsulation and co-encapsulation of 2 or 3 cell types in a single droplet.

The devices can be fabricated by standard soft lithography techniques and treated with a material or coating such as Aquapel, available from PPG Industries, to make the surfaces hydrophobic and allow smooth droplet generation. The cell-containing droplets can be docked in the microarray for automated live-cell imaging. The design of microfluidic chip can be optimized to enable testing of multiple conditions as required for cell therapy screening applications.

Droplet generation and liquid handling can be performed using approaches that have been proven to work using single chip systems. The droplets then enter the incubation array part of the chip. The oil and cell microchannel lengths, diameters, and other parameters can be calculated to ensure equal or substantially equal flow resistance to the array in each unit. The parameters that can be optimized to provide substantially equal flow resistance include material, flow profile, pressure drop, mixing efficiency and droplet generation performance, as well as channel dimensions, i.e., length and diameter. The parameters can be selected to the substantially identical for each channel, or can be adjusted to account for variations, to provide a substantially equal flow resistance in each channel. For example, in some aspects, channels may have different lengths, and other parameters, such as diameter, can be adjusted to account for the differing lengths. The present design can simplify the number of oil inlets required and create channels with unified flow resistance for synchronous generation of droplets with the same dimensions/volumes.

A further aspect of the present technology is the incorporation of high-throughput microdroplet sorting, which can be used for enrichment of desired cell types or heterotypic cell pairs or other groupings of cells and additionally to separate subgroups of droplets by functionality into separate channels. The process of single-cell encapsulation in droplets is inherently stochastic, and the rate of co-encapsulation of two different cell types in droplets can be less than optimal, such as 10-13% of the droplets. This limitation can be overcome using a high-throughput (18,000 events/s), multi-color droplet sorting system for the enrichment of droplets of interest (DOI).

In some aspects, a merging junction can be employed to introduce an additional component into the microdroplets to form merged microdroplets. For example, a secondary reagent can be added to the microdroplets to study additional cell functions and behaviors, or a lysing buffer can be added to prepare the microdroplets for sequencing.

Figure 3A:
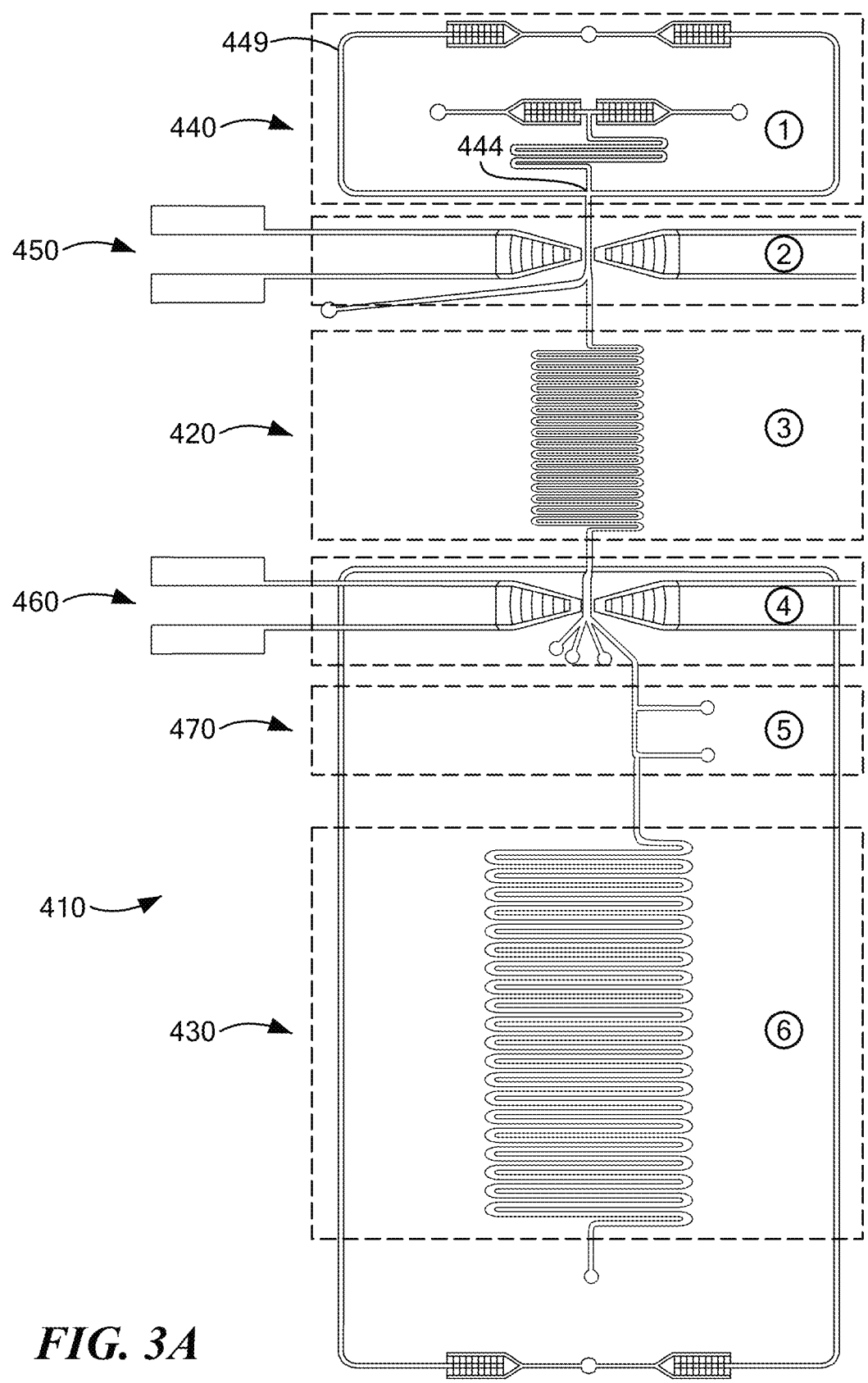
FIG. 3A is a schematic illustration of an aspect of a multiplex microfluidic system incorporating (1) a droplet generator, (2) an upstream droplet sorter (first sorter); (3) an upstream docking array (first microdroplet incubation chamber); (4) a downstream multiplex droplet sorter (second sorter); (5) a merging junction; and (6) a downstream docking array (second microdroplet incubation chamber).
Figure 3B:
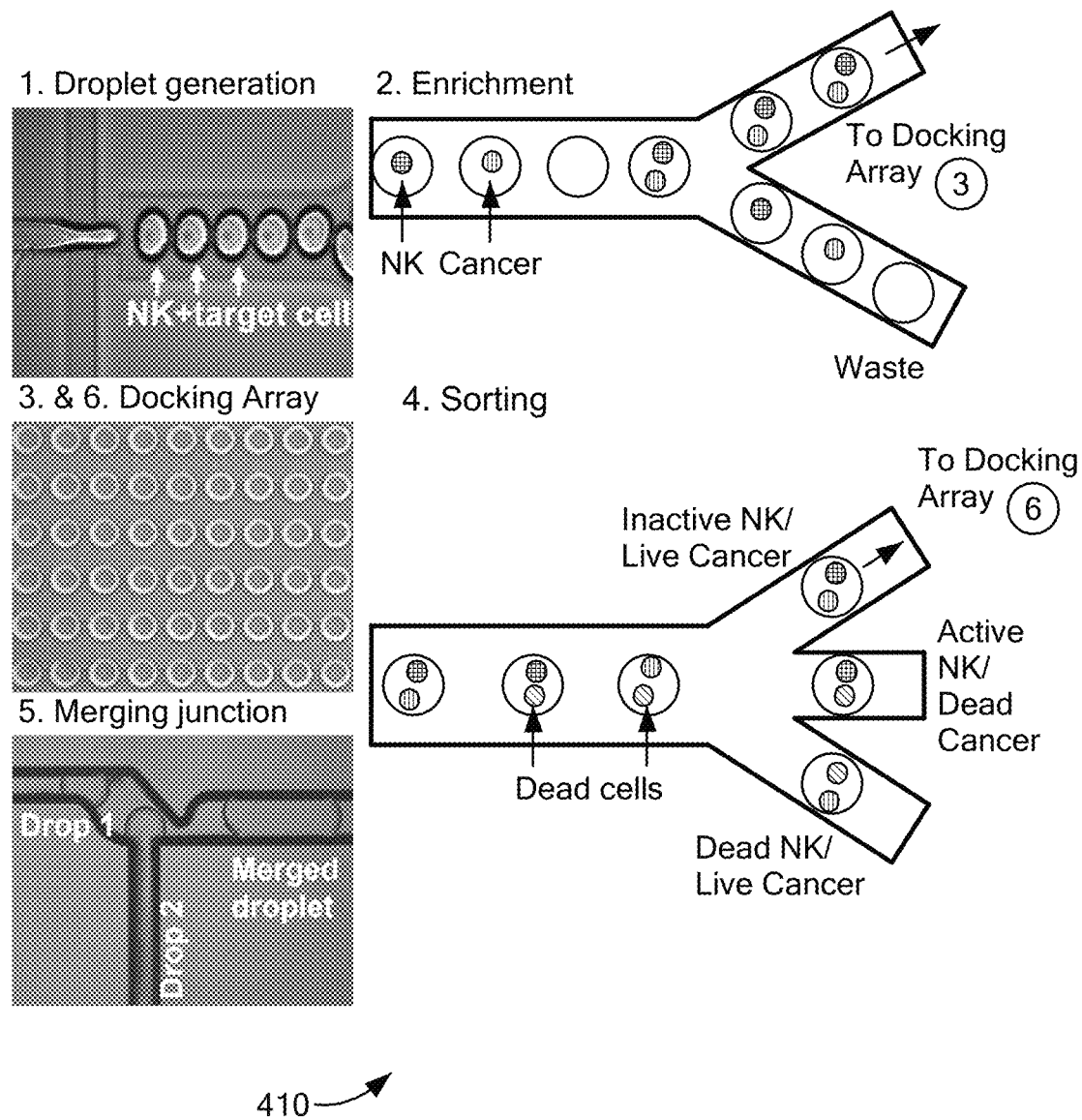
FIG. 3B is a schematic flow diagram including a series of images of droplet generation, a docking array, and a merging junction of the multiplex microfluidic system of FIG. 3A illustrating droplet enrichment and multiplex sorting.
Figure 3C:
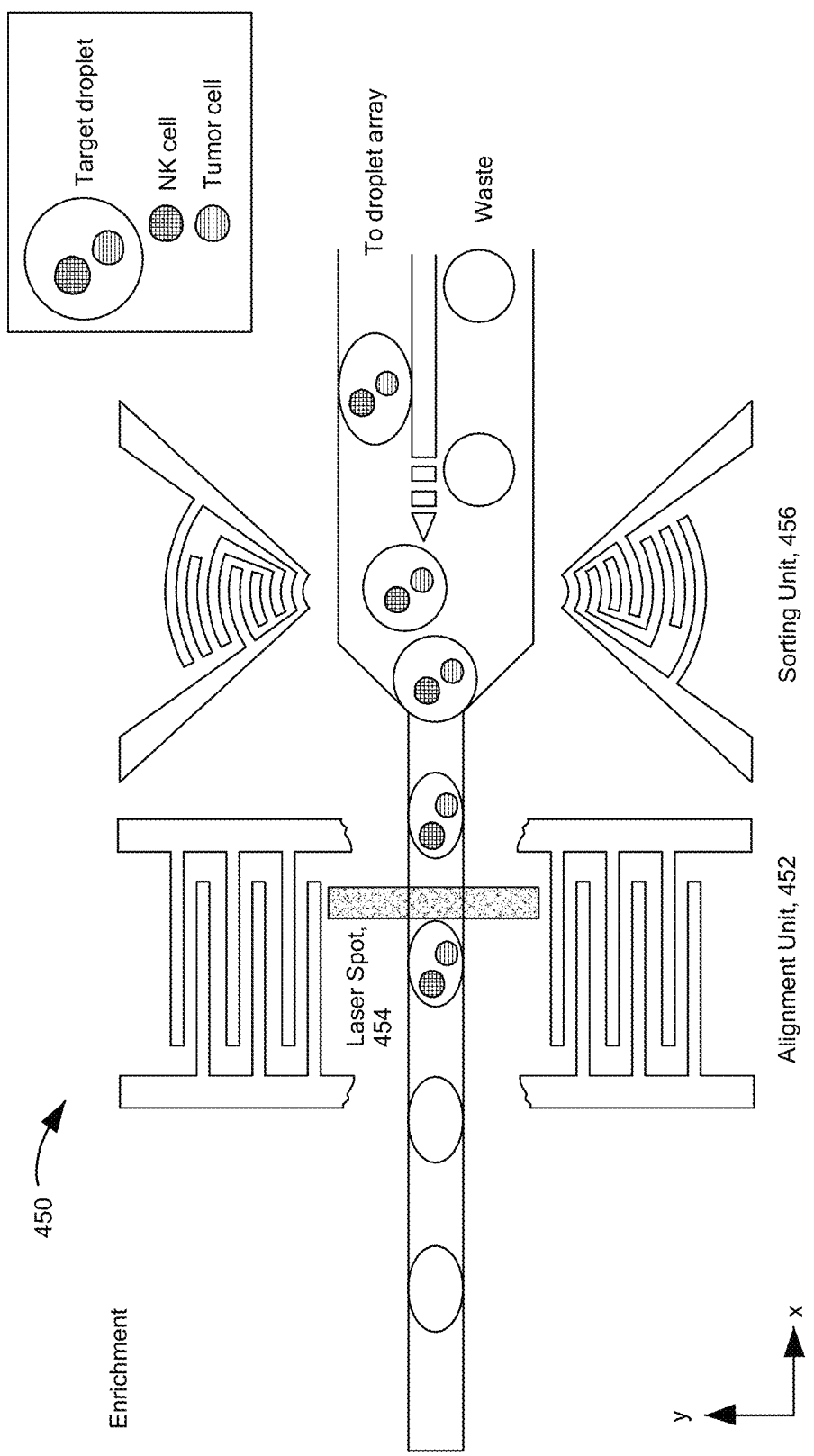
FIG. 3C is a schematic illustration of an upstream sorter for droplet enrichment of the system of FIG. 3A.
Figure 3D:
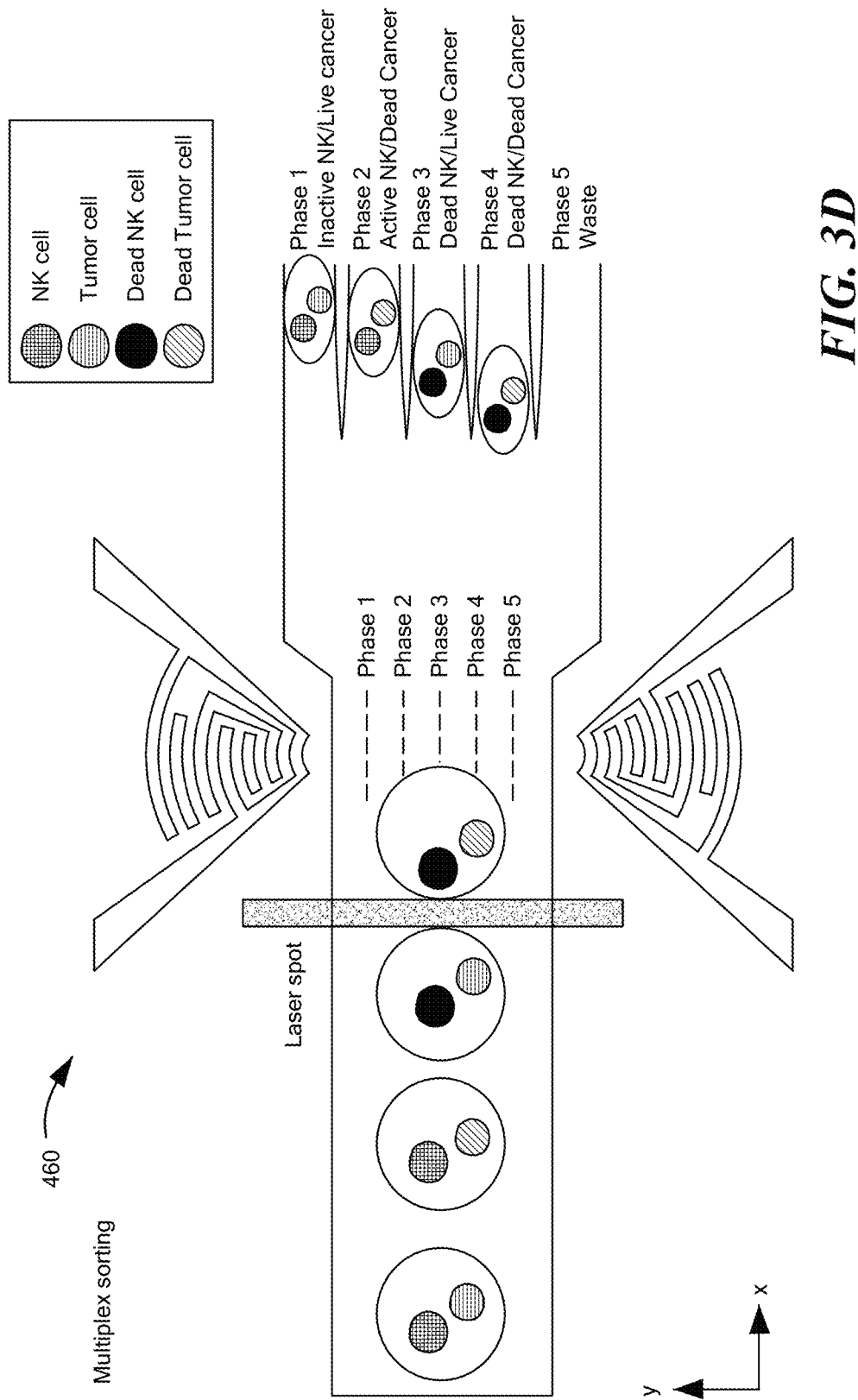
FIG. 3D is a schematic illustration of a downstream multiplex droplet sorter of the system of FIG. 3A.

Referring to FIGS. 3A and 3B, an integrated microdroplet sorter system 410 can be provided. The system can employ an upstream microfluidic device 420 including an incubation chamber and a downstream microfluidic device 430 including an incubation chamber, as described above. A combination 440 of microchannel networks 442 and droplet formation junction 444, as described above, can be used to generate microdroplets, indicated at step 1. Prior to introduction into the upstream microfluidic device, an enrichment sorter 450 can be used to separate droplets of interest from droplets not of interest, indicated at step 2. FIG. 3C shows detail of an embodiment of enrichment sorter 450, depicting alignment unit 452 and sorting unit 456. For example, microdroplets that contain both an NK cell and a cancer cell, which are droplets of interest, can be directed into a microchannel to a docking array of the upstream microfluidic device 420. Microdroplets that only contain one cell, such as only an NK cell or only a cancer cell, or droplets that do not contain any cells, can be diverted to waste. See step 2. The droplets of interest can then be incubated in the docking array of the upstream microfluidic device, as indicated at step 3.

After the desired incubation period, the microdroplets can be discharged from the upstream microfluidic device 420. A multiplex sorter 460 can be used to separated droplets by functionality, indicated at step 4. For example, microdroplets can contain various cell combinations, such as inactive NK/live cancer, active NK/dead cancer; dead NK/live cancer, and dead NK/dead cancer. Each of these combinations can be sorted for diversion to an appropriate location, which can be a downstream microfluidic device 430, indicated at step 6.

Downstream of the multiplex sorter, additional components can be merged into one of the microdroplet streams prior to introduction into the downstream microfluidic device. For example, a merging junction 470 can be provided to merge one droplet with a new, incoming droplet, indicated at step 5. For example, a merging junction can incorporate a constriction through which two droplets pass, resulting in a merged droplet. Merging junctions are described in US 2018/0203005, incorporated herein by reference.

The merged droplets can then be introduced into the downstream microfluidic device, which can be larger than the upstream microfluidic device to accommodate the larger volume due to the introduction of the additional component to form the merged droplets.

Any suitable sorting technology can be used. For example, in some aspects the present technology can employ an acoustofluidic sorter and fluorescence-activated droplet sorter (FADS). Furthermore, two sorters can be combined in a single device to increase functionality. This sorter technology makes it possible to enrich an array in droplets containing heterotypic single cells or cell clusters (e.g., one NK cell, four tumor cells) as well as identify and separate subgroups of cells with distinct functionality. The sorter can operate at a frequency and power intensity ranges similar to those of widely-used ultrasonic imaging devices. This biocompatible sorting process can minimize disruption of cell function and maximize survival, an important consideration for dynamic evaluation of cell-cell interaction, cell activity and subsequent genomic profiling.

Single cell analytical tools such as described herein can provide useful insights into the genetic, phenotypic and induced heterogeneity into healthy and diseased cells. The correlation of molecular analysis with quantitative evaluation of cell behaviors (such as motility, secretion, signaling, and epigenetic modification) at single-cell level is a powerful approach to identify disease signatures. In particular, single cell analysis can assist in revealing, and ultimately utilizing, patient-specific cell data to devise a more personalized approach to therapeutic regimens. This is a challenge in modern medicine, since there is significant inter-patient and even intra-patient variability (during and after therapy) in response to well-established drug cocktails, which can frequently lead to acquired therapeutic resistance over a period of time. With the emergence of a number of new types of treatment, including cell-based immunotherapies, single cell analysis tools such as described herein can be used as preclinical and/or experimental in vitro models in helping devise, validate and optimize treatment protocols for a specific patient using diseased cells from the very same patient. Such an approach can aid in understanding the complexities of donor-host cell interactions prior to administering cell-based transfusions.

Figure 4:
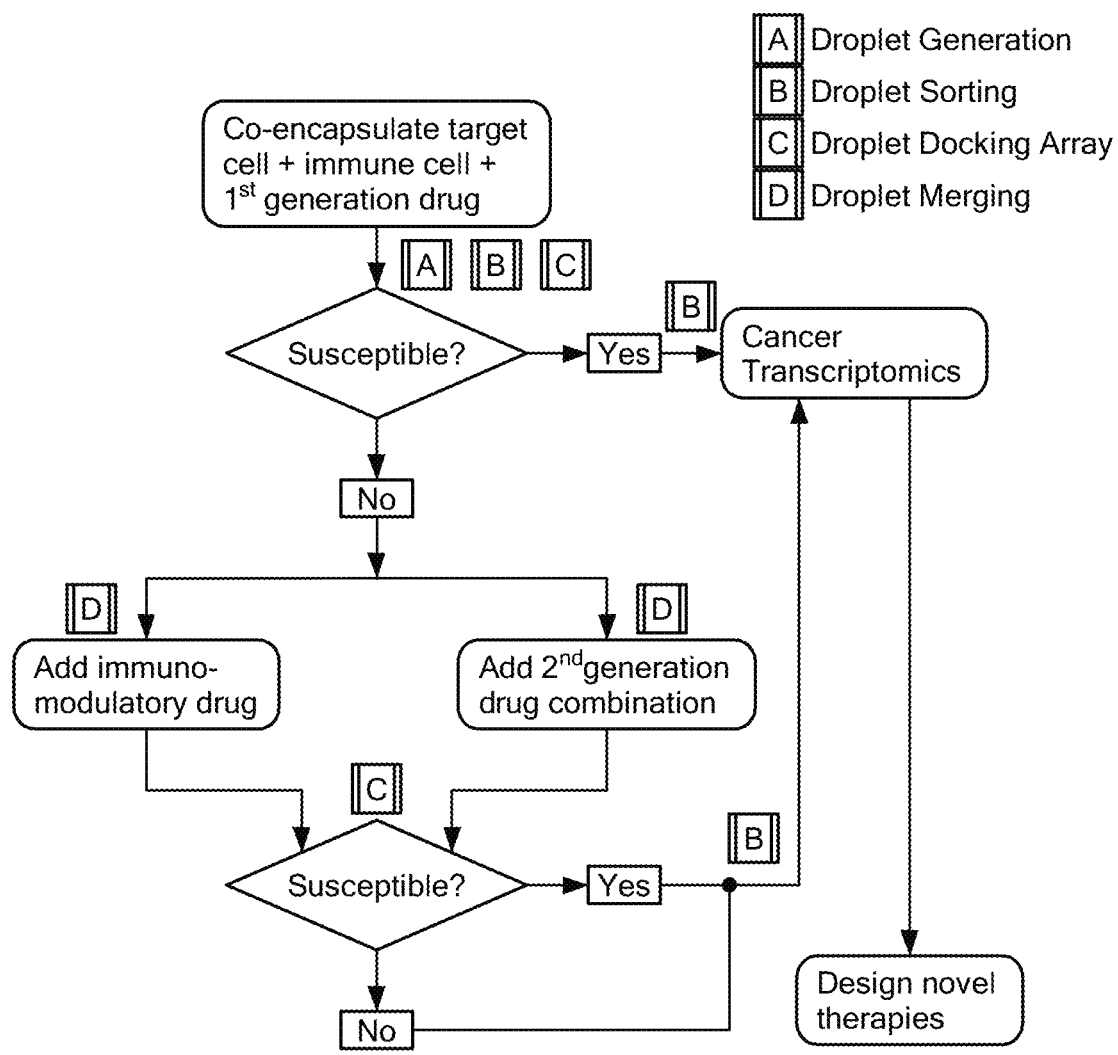
FIG. 4 is a flow diagram of a method of using a multiplex microfluidic system.
Figure 5:
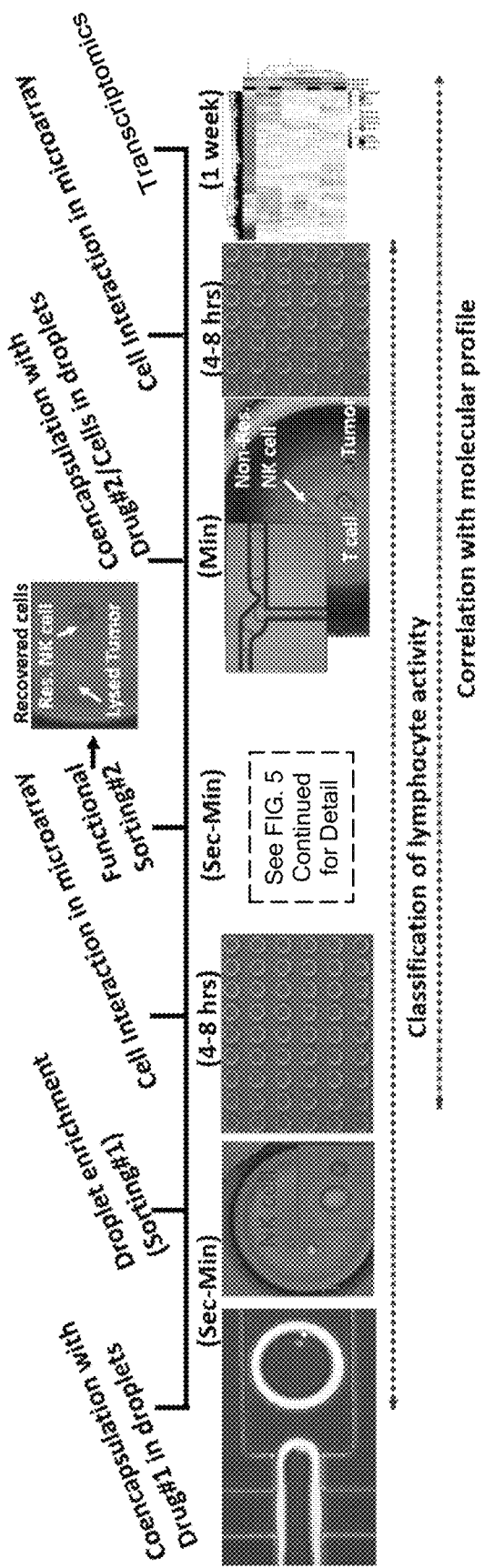
FIG. 5 is a schematic flow diagram including a series of images of a method of using a illustration of a multiplex microfluidic system.
Figure 5:
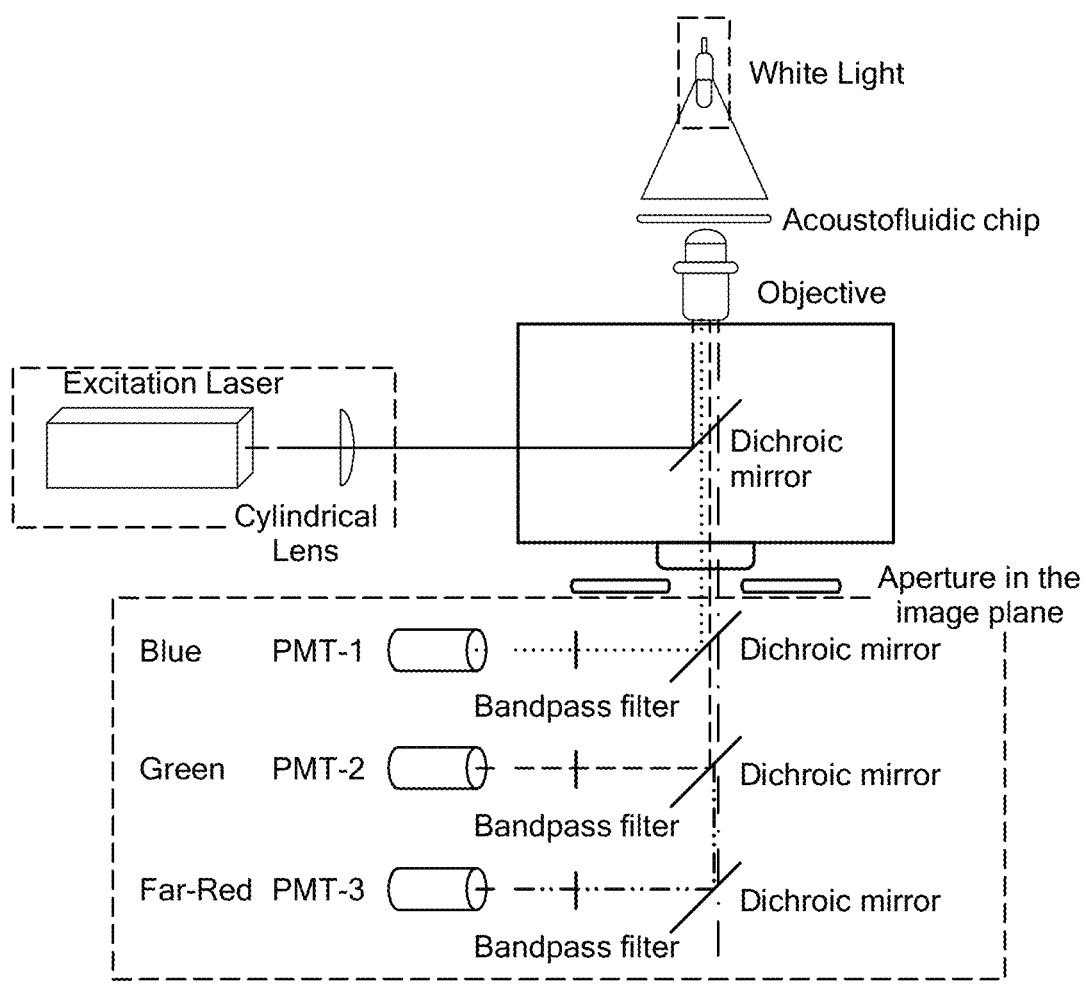
Figure 6:
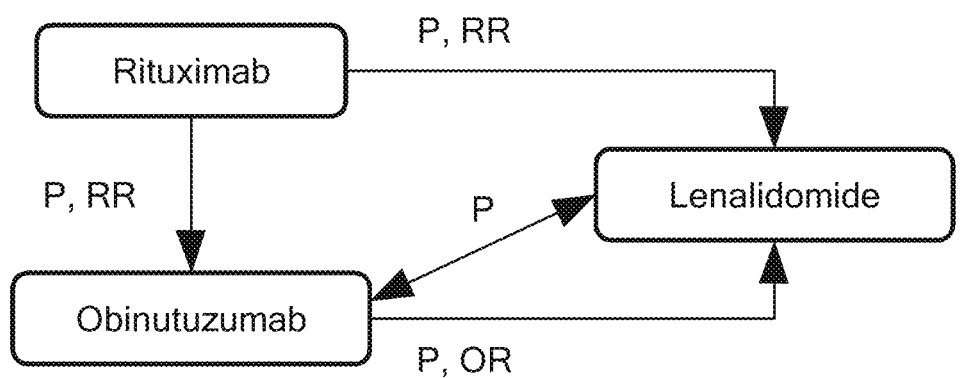
FIG. 6 is a schematic of an example of antibody and drug combinations that can be tested on various types of lymphoma cells, in which the directionality of the arrows indicates the order of drugs to be applied and the double-sided arrow indicates that both drugs are to be applied simultaneously.

For example, FIG. 4 illustrates in flow chart form of the use of a system such as that described above, which can be used for a clinical decision-making process. FIG. 5 illustrates an explmplary use of the system with a series of images. Referring to FIGS. 4 and 5, a target cell (for example, a cancer cell) an immune cell (for example, an NK cell), and a first generation drug are co-encapsulated in microdroplets (indicated by the letter A). The droplets are sorted, via an enrichment sorter (B), and introduced into a droplet docking array (C). Upon incubation in the docking array, a determination can be made of those microdroplets which indicated susceptibility to the drug. For example, fluorescence detection or other techniques can be used to analyze the microdroplets. The susceptible droplets can be sorted out, via a multiplex sorter, and diverted to, for example, a cancer transcriptomics process, leading potentially to novel therapies. The microdroplets that do not indicate susceptibility can be sorted out for introduction to a downstream microfluidic device. Prior to introduction to the device, a further component, such as an immunomodulatory drug or a second generation drug combination, can be merged into the microdroplets (D). Upon introduction into the droplet docking array (C) and incubation, a further determination of susceptibility can be made and appropriate sorting (B) of those microdroplets indicated susceptibility can be performed, for diversion to the cancer transcriptomics process.

Known prior art methods of cellular classification employ the top-down approach (interrogating proteomics or genomics directly), thereby destroying the cell, which does not allow the possibility of using the same cell to correlate genomics with functional assays. The present technology provides a bottom-up method of classification (see FIG. 5), by first conducting functional phenotyping of cells and then probing the underlying biology in these subsets of cells via systems-level analysis. This approach can allow for a comprehensively determined biological basis of immunotherapeutic efficacy in a given cellular system.

The present system incorporates several technical features or aspects not available in currently known microfluidic devices.

In some aspects, the technology can provide grading of the efficiency of anti-tumor activity by on-chip drug screening in large-scale droplet microarray. Multiple droplet sorters can be consolidated with a high throughput droplet microarray to provide an integrated platform for functional microfluidic imaging cytometry. The sorted, enriched DOIs can be stably arrested in a droplet docking array having, for example, 10,000 sites, and imaged rapidly to detect dynamic interactive cellular functions. This approach can provide critical information about cell kinetics and allow the development of predictive classifiers for phenotypic screening. For instance, effector immune cells kill target cancer cells through direct contact, but the efficacy of such activity could either be 'fast' or 'slow' depending on inherent sensitivity to immune cells, drugs and microenvironment. This translates to "responsive" or "nonresponsive" cancer cells. The present system can be used to can grade the efficiency of a particular therapeutic protocol by assessing the degree of sensitivity of the cancer cells. Dynamic features in cancer cell response can be identified that can then facilitate "tuning" the cell behavior in a desired direction.

Moreover, by incorporating a robust droplet merging junction along with the dual droplet microarrays, additional therapies, such as immunomodulatory drugs or cell-based vaccines, can be introduced into the intact droplets at delayed time-points. This allows altering of the droplet microenvironment and potentially allows switching immune cell activity.

In a further aspect, the system can be used to correlate cell response with genomic analysis to determine subset-specific molecular signatures. Understanding the associated links between cancer-immune cell interaction and immunotherapeutic resistance can be useful in making appropriate clinical decisions and identifying potential drug combinations the provide long-lasting benefit to patients. The technology sorts functionally distinct cell types so that the recovered cells can be subjected to transcriptomic analyses. In this manner, it can be possible to determine genetic profiles of cancer cells with differential immune cell- and drug-sensitive activities. Thus, such determinations can be used to discover immunomodulatory drug combinations that could potentially maximize NK cell-mediated killing of cancer targets and help streamline treatment protocols.

In some aspects, the present microfluidic-droplet based technology can be used for capturing, manipulating and sorting cells for phenotypic drug screening applications. Thus, the droplet-based microanalytical system can be used to interrogate dynamic effector-immune cell responses, to assess drug susceptibility of target (e.g., lymphoma) cells, and to sort functionally distinct immune cell subsets. In some aspects, the system can provide a high-throughput, multi-channel droplet sorting technique for the rapid enrichment of droplets containing single NK cell and four tumor cells. In some aspects, an integrated platform can be provided that allows the monitoring of kinetics and efficacy of cancer cell killing as a result of the 'priming' immunoregulatory interaction with the selective isolation of cells from different phenotypic sub-populations to perform downstream genetic analysis. In some aspects, the microanalytical system can allow the assessment of thousands single NK-cancer cell droplets so that statistically relevant conclusions can be drawn regarding interactive dynamics and cell cytotoxicity at single cell level. In some aspects, correlation of functional phenotypes with downstream transcriptomic analysis can be determined.

In some aspects, the system can provide a high-purit, high-throughput, multi-channel droplet sorting unit. The system can include a sorting device or module with two segments: (a) an upstream sorter that can be used to specifically select droplets containing the desired heterotypic cell pairs (for example, one NK and four tumor cells), and (b) a downstream sorter that can be used to detect and sort droplets containing 'responsive' and 'non-responsive' NK cells at the end of the experimental duration.

What is claimed is:

1. A multiplex microfluidic system for analyzing cells in microdroplets, comprising:
   a chip comprising a plurality of microfluidic devices, each device comprising a microdroplet incubation chamber;
   an oil supply microchannel network in the chip comprising a plurality of microchannel branches fluidically connecting an inlet connectable to an oil supply and two or more of the microfluidic devices in the chip, the microchannel branches having substantially equal flow resistance;
   a cell supply microchannel network in the chip comprising a plurality of microchannel branches fluidically connecting one or more cell supply inlets connectable to a cell supply and two or more of the microfluidic devices in the chip, the microchannel branches having substantially equal flow resistance; and
   a plurality of droplet formation junctions in the chip, each droplet formation junction associated with one of the microfluidic devices and configured to produce aqueous microdroplets suspended in oil for delivery to the microdroplet incubation chamber, the aqueous microdroplets comprising at least one cell, each droplet formation junction comprising an intersection between one of the oil supply microchannel branches and at least one of the cell supply microchannel branches and an outgoing microchannel in fluid communication with the microdroplet incubation chamber.

2. The system of claim 1, wherein each of the microchannel branches of the cell supply microchannel network has one or more parameters that are the same, the parameters selected from the group consisting of a length of the microchannel from the inlet to the droplet formation junction, a diameter of the microchannel from the inlet to the droplet formation junction, a material of the microchannel wall from the inlet to the droplet formation junction, a channel profile of the microchannel from the inlet to the droplet formation junction, and a pressure drop along the microchannel from the inlet to the droplet formation junction.

3. The system of claim 1, wherein each of the microchannel branches of the oil supply microchannel network has one or more parameters that are the same, the parameters selected from the group consisting of a length of the microchannel from the inlet to the droplet formation junction, a diameter of the microchannel from the inlet to the droplet formation junction, a material of the microchannel wall from the inlet to the droplet formation junction, a channel profile of the microchannel from the inlet to the droplet formation junction, and a pressure drop along the microchannel from the inlet to the droplet formation junction.

4. The system of claim 1, wherein the intersection of each droplet formation junction is disposed between at least one of the oil supply microchannel branches and at least two of the cell supply microchannel branches, and wherein the outgoing microchannel is in fluid communication with the microdroplet incubation chamber.

5. The system of claim 1, further comprising a cell suspension fluidically connected with the one or more cell supply inlets, wherein the cell suspension comprises a cell type selected from tumor cells, immune cells, natural killer cells, T cells, B cells, dendrocytes, macrophages, and bacterial cells.

6. The system of claim 1, further comprising a plurality of different cell supply inlets, each in fluid communication with one or more additional microchannel branches of substantially equal flow resistance, each branch intersecting at an upstream junction with associated ones of the branches of the cell supply microchannel network upstream of the droplet formation junction with the oil supply microchannel branches.

7. The system of claim 6, further comprising a first cell suspension fluidically connected with the one or more cell supply inlets and a second cell suspension fluidically connected to the additional cell supply microchannel network, wherein each of the first and second cell suspensions comprises a cell type selected from the group consisting of tumor cells, immune cells, natural killer cells, T cells, B cells, dendrocytes, macrophages, and bacterial cells.

8. The system of claim 1, further comprising a reagent supply microchannel network in fluid communication with at least two reagent solutions having different reagent concentrations, the reagent supply microchannel network comprising a mixing pathway of interconnected microchannels to provide mixtures having different reagent concentrations, the interconnected microchannels intersecting at upstream junctions with the microchannel branches of the cell supply microchannel network upstream of the droplet formation junction with the oil supply microchannel branches.

9. The system of claim 1, wherein the oil supply microchannel network includes a single oil supply inlet formed in the chip, and each of the microchannel branches of the oil supply microchannel network extends through the chip from the single oil supply inlet to an associated one of the droplet formation junctions.

10. The system of claim 1, wherein the oil supply microchannel network includes a plurality of oil supply inlets formed in the chip, and at least two microchannel branches of the oil supply microchannel network extend through the chip from one of the plurality of oil supply inlets.

11. The system of claim 1, wherein the incubation chamber comprises an array of single microdroplet chambers or an array of microdroplet docking stations.

12. The system of claim 1, comprising at least six of the microfluidic devices.

13. The system of claim 1, comprising at least eight of the microfluidic devices.

14. The system of claim 1, further comprising a microdroplet sorter on a microchannel of at least one of the microfluidic devices, the sorter configured to sort microdroplets from the microfluidic device into at least a first subgroup of microdroplets having a first characteristic and a second subgroup of microdroplets having a second characteristic.

15. The system of claim 14, wherein said first and second characteristics are selected from the presence or absence of one or more cell types or cell combinations, the presence of one or more cell biomarkers, living or dead cell condition, cell staining, and cell morphology.

16. The system of claim 14, wherein said microdroplet sorter is configured to direct said first and second subgroups of microdroplets into different downstream microdroplet incubation chambers.

17. The system of claim 14, wherein the microdroplet sorter is configured to deliver microdroplets of interest to the microdroplet incubation chamber or to another on chip or off chip microfluidic device, and to direct microdroplets not of interest to a waste pathway.

18. The system of claim 17, wherein microdroplets of interest are directed to the microdroplet incubation chamber, further comprising a second microdroplet sorter downstream of said microdroplet incubation chamber and configured to sort microdroplets exiting the microdroplet incubation chamber according to one or more cell characteristics, and to direct the microdroplets to a merging junction configured to merge the microdroplets with microdroplets containing a reagent or cell of interest, to a second microdroplet incubation chamber, or to a collection port.

19. The system of claim 1, further comprising a merging junction configured to merge microdroplets in a microchannel of a microfluidic device with microdroplets containing a reagent or cell of interest.

20. A method of multiplex analysis of single cell characteristics, the method comprising:
(a) providing the multiplex microfluidic system of claim 1, an oil, at least a first suspension of single cells, and optionally at least a first reagent;
(b) flowing the oil and the cell suspension into their respective inlets in the chip, so as to form two or more streams of aqueous microdroplets in the oil at the droplet formation junctions of the chip, at least a portion of the microdroplets containing one or more cells per microdroplet, whereby the microdroplets enter respective microdroplet incubation chambers of the microfluidic devices;

(c) incubating the microdroplets in the microdroplet incubation chambers to allow expression of one or more cell characteristics of cells within the microdroplets; and (d) analyzing said single cell characteristics by observing the microdroplets during step (c).

21. A microdroplet sorting and analysis chip comprising:

an oil supply microchannel fluidically connecting an oil supply inlet to a droplet formation junction configured to form a plurality of aqueous microdroplets;

a cell supply microchannel fluidically connecting one or more cell supply inlets to the droplet formation junction;

a first microdroplet sorter disposed downstream of the droplet formation junction, the first microdroplet sorter configured to sort microdroplets from the droplet formation junction according to one or more characteristics of cells present in the microdroplets, wherein the sorted microdroplets are diverted into one of two or more microchannels exiting the first sorter;

a first microdroplet incubation chamber disposed downstream of one or more of the microchannels exiting the first sorter;

a second microdroplet sorter disposed downstream of the first microdroplet incubation chamber, the second sorter configured to sort microdroplets exiting the first microdroplet incubation chamber according to one or more characteristics of cells present in the microdroplets, wherein the sorted microdroplets are diverted into one of two or more microchannels exiting the second sorter;

an optional microdroplet merging junction configured to merge at least a portion of the microdroplets obtained from the second sorter with aqueous microdroplets comprising a reagent and/or additional cells;

a second microdroplet incubation chamber disposed downstream of one or more of the microchannels exiting the second sorter or downstream of the microdroplet merging junction, if present.

22. A method of sorting and analyzing cells in microdroplets, the method comprising:

(a) providing the microdroplet sorting and analysis chip of claim 21, an oil, at least a first suspension of single cells, and optionally at least a first reagent and/or a suspension of additional single cells;

(b) flowing the oil and the first cell suspension into their respective inlets in the chip, so as to form a stream of aqueous microdroplets in the oil at the droplet formation junction, at least a portion of the microdroplets containing one or more cells per microdroplet;

(c) sorting the microdroplets from (b) at the first sorter according to one or more characteristics of cells in the microdroplets, whereby at least a portion of the microdroplets flow into the first microdroplet incubation chamber;

(d) incubating the microdroplets in the first microdroplet incubation chamber to allow expression of one or more cell characteristics of cells within the microdroplets;

(e) analyzing said single cell characteristics by observing the microdroplets during step (d);

(f) flowing the microdroplets from the first microdroplet incubation chamber to the second sorter and sorting the microdroplets using the second sorter according to one or more characteristics of cells in the microdroplets, whereby (i) at least a portion of the microdroplets flow into the optional droplet merging junction and merge with microdroplets containing said first reagent and/or said suspension of additional single cells and the merged droplets flow into the second microdroplet incubation chamber, or (ii) at least a portion of the microdroplets flow into the second microdroplet incubation chamber;

(g) incubating the microdroplets in the second microdroplet incubation chamber to allow expression of one or more characteristics of cells within the microdroplets; and (h) analyzing said cell characteristics by observing the microdroplets during step (g).

* * * * *